(12) United States Patent
Nohr et al.

(10) Patent No.: US 6,368,396 B1
(45) Date of Patent: Apr. 9, 2002

(54) COLORANTS, COLORANT STABILIZERS, INK COMPOSITIONS, AND IMPROVED METHODS OF MAKING THE SAME

(75) Inventors: Ronald Sinclair Nohr, Alpharetta; John Gavin MacDonald, Decatur, both of GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/490,294

(22) Filed: Jan. 19, 2000

Related U.S. Application Data

(60) Provisional application No. 60/116,315, filed on Jan. 19, 1999, and provisional application No. 60/121,301, filed on Feb. 23, 1999.

(51) Int. Cl.$^7$ .......................... C09D 11/00; C09B 47/00; C07D 487/22
(52) U.S. Cl. .............................. 106/31.49; 106/31.78; 540/145
(58) Field of Search ........................... 106/31.49, 31.78; 540/145

(56) References Cited

U.S. PATENT DOCUMENTS

| | | |
|---|---|---|
| 575,228 A | 1/1897 | von Gallois |
| 582,853 A | 5/1897 | Feer |
| 893,636 A | 7/1908 | Maywald |
| 1,013,544 A | 1/1912 | Fuerth |
| 1,325,971 A | 12/1919 | Akashi |
| 1,364,406 A | 1/1921 | Olsen |
| 1,436,856 A | 11/1922 | Brenizer et al. |
| 1,744,149 A | 3/1930 | Staehlin |
| 1,803,906 A | 5/1931 | Krieger et al. |
| 1,844,199 A | 2/1932 | Bicknell et al. |
| 1,876,880 A | 9/1932 | Drapal |
| 1,880,572 A | 10/1932 | Wendt et al. |
| 1,880,573 A | 10/1932 | Wendt et al. |
| 1,916,350 A | 7/1933 | Wendt et al. |
| 1,916,779 A | 7/1933 | Wendt et al. |
| 1,955,898 A | 4/1934 | Wendt et al. |
| 1,962,111 A | 6/1934 | Bamberger |
| 2,005,378 A | 6/1935 | Kiel |
| 2,005,511 A | 6/1935 | Stoll et al. |
| 2,049,005 A | 7/1936 | Gaspar |
| 2,054,390 A | 9/1936 | Rust et al. |
| 2,058,489 A | 10/1936 | Murch et al. |
| 2,062,304 A | 12/1936 | Gaspar |
| 2,090,511 A | 8/1937 | Crossley et al. |
| 2,097,119 A | 10/1937 | Eggert |
| 2,106,539 A | 1/1938 | Schnitzspahn |
| 2,111,692 A | 3/1938 | Saunders et al. |
| 2,125,015 A | 7/1938 | Gaspar |
| 2,130,572 A | 9/1938 | Wendt |
| 2,132,154 A | 10/1938 | Gaspar |
| 2,145,960 A | 2/1939 | Wheatley et al. |
| 2,154,996 A | 4/1939 | Rawling |
| 2,159,280 A | 5/1939 | Mannes et al. |
| 2,171,976 A | 9/1939 | Erickson |

(List continued on next page.)

FOREIGN PATENT DOCUMENTS

| | | |
|---|---|---|
| AU | 103085 | 4/1937 |
| AU | 12624/88 | 9/1988 |
| BE | 620075 | 5/1962 |
| BE | 637169 | 3/1964 |
| CA | 413257 | 10/1932 |

OTHER PUBLICATIONS

Chem abstract of 115: 182921, 1991, no month available.*

Noguchi, H. UV Curable, Aqueous Ink Jet Ink: Material Design and Performance for Digital and Performance for Digital Printing *1998 International Conf. on Digital Printing Technologies* 107–110 1998, no month available.

ESP@CENET databse JP 10324836 (Omron Corp.), Dec. 8, 1998. abstract 1998.

Wang et al. Effects of substituenta attached at benzaldehyde on the synthesis and properties of porphyrins *Chem Abstracts* 113(1996, 9) no month available.

Derwent World Patents Index JP 8002092 (Mitsubishi Paper Mills Ltd.) Jan. 9, 1996. abstract 1996.

(List continued on next page.)

Primary Examiner—Helene Klemanski
(74) Attorney, Agent, or Firm—Kilpatrick Stockton LLP

(57) ABSTRACT

The present invention relates to a family of new porphine compounds for use as colorants and/or colorant stabilizers. The new porphine compounds may be used alone as a magenta dye or may be used in combination with one or more colorants to provide light stability to colorants. The present invention further relates to inks containing the new porphine compounds and a method for making the new compounds. The present invention also relates to improved methods of making Cu-meso-tetra-(2-sulfanatophenyl)-porphine (designated o-CuTPPS4). The improved processes allow the production of o-CuTPPS4 at lower cost and higher yields compared to conventional methods of making o-CuTPPS4. The present invention further relates to the use of o-CuTPPS4 as a colorant stabilizer for a variety of colorants, especially magenta colorants. The o-CuTPPS4, according to the present invention, provides a more stable and more "blue" colorant stabilizer compared to known colorant stabilizers, such as Cu-meso-tetra-(p-phenylcarboxylic acid)-porphine.

31 Claims, No Drawings

U.S. PATENT DOCUMENTS

| | | |
|---|---|---|
| 2,181,800 A | 11/1939 | Crossley et al. |
| 2,185,153 A | 12/1939 | Lecher et al. |
| 2,220,178 A | 11/1940 | Schneider |
| 2,230,590 A | 2/1941 | Eggert et al. |
| 2,237,885 A | 4/1941 | Markush et al. |
| 2,243,630 A | 5/1941 | Houk et al. |
| 2,268,324 A | 12/1941 | Polgar |
| 2,281,895 A | 5/1942 | van Poser et al. |
| 2,328,166 A | 8/1943 | Poigar et al. |
| 2,346,090 A | 4/1944 | Staehle |
| 2,349,090 A | 5/1944 | Haddock |
| 2,356,618 A | 8/1944 | Rossander et al. |
| 2,361,301 A | 10/1944 | Libby, Jr. et al. |
| 2,364,359 A | 12/1944 | Kienle et al. |
| 2,381,145 A | 8/1945 | von Glahn et al. |
| 2,382,904 A | 8/1945 | Federsen |
| 2,386,646 A | 10/1945 | Adams et al. |
| 2,402,106 A | 6/1946 | von Glahn et al. |
| 2,416,145 A | 2/1947 | Biro |
| 2,477,165 A | 7/1949 | Bergstrom |
| 2,527,347 A | 10/1950 | Bergstrom |
| 2,580,461 A | 1/1952 | Pearl |
| 2,601,669 A | 6/1952 | Tullsen |
| 2,612,494 A | 9/1952 | von Glahn et al. |
| 2,612,495 A | 9/1952 | von Glahn et al. |
| 2,628,959 A | 2/1953 | von Glahn et al. |
| 2,647,080 A | 7/1953 | Joyce |
| 2,680,685 A | 6/1954 | Ratchford |
| 2,728,784 A | 12/1955 | Tholstrup et al. |
| 2,732,301 A | 1/1956 | Robertson et al. |
| 2,744,103 A | 5/1956 | Koch |
| 2,757,090 A | 7/1956 | Meugebauer et al. |
| 2,763,550 A | 9/1956 | Lovick |
| 2,768,171 A | 10/1956 | Clarke et al. |
| 2,773,056 A | 12/1956 | Helfaer |
| 2,798,000 A | 7/1957 | Monterman |
| 2,809,189 A | 10/1957 | Stanley et al. |
| 2,827,358 A | 3/1958 | Kaplan et al. |
| 2,834,773 A | 5/1958 | Scalera et al. |
| 2,875,045 A | 2/1959 | Lurie |
| 2,892,865 A | 6/1959 | Giraldi et al. |
| 2,897,187 A | 7/1959 | Koch |
| 2,936,241 A | 5/1960 | Sharp et al. |
| 2,940,853 A | 6/1960 | Sagura et al. |
| 2,955,067 A | 10/1960 | McBurney et al. |
| 2,992,129 A | 7/1961 | Gauthier |
| 2,992,198 A | 7/1961 | Funahashi |
| 3,030,208 A | 4/1962 | Schellenberg et al. |
| 3,071,815 A | 1/1963 | MacKinnon |
| 3,075,014 A | 1/1963 | Palopoli et al. |
| 3,076,813 A | 2/1963 | Sharp |
| 3,104,973 A | 9/1963 | Sprague et al. |
| 3,114,634 A | 12/1963 | Brown et al. |
| 3,121,632 A | 2/1964 | Sprague et al. |
| 3,123,647 A | 3/1964 | Duennenberger et al. |
| 3,133,049 A | 5/1964 | Hertel et al. |
| 3,140,949 A | 7/1964 | Sprague et al. |
| 3,154,416 A | 10/1964 | Fidelman |
| 3,155,509 A | 11/1964 | Roscow |
| 3,175,905 A | 3/1965 | Wiesbaden |
| 3,178,285 A | 4/1965 | Anderau et al. |
| 3,238,163 A | 3/1966 | O'Neill |
| 3,242,215 A | 3/1966 | Heitmiller |
| 3,248,337 A | 4/1966 | Zirker et al. |
| 3,266,973 A | 8/1966 | Crowley |
| 3,282,886 A | 11/1966 | Gadecki |
| 3,284,205 A | 11/1966 | Sprague et al. |
| 3,300,314 A | 1/1967 | Rauner et al. |
| 3,304,297 A | 2/1967 | Wegmann et al. |
| 3,305,361 A | 2/1967 | Gaynor et al. |
| 3,313,797 A | 4/1967 | Kissa |
| 3,320,080 A | 5/1967 | Mazzarella et al. |
| 3,330,659 A | 7/1967 | Wainer |
| 3,341,492 A | 9/1967 | Champ et al. |
| 3,359,109 A | 12/1967 | Harder et al. |
| 3,361,827 A | 1/1968 | Biletch |
| 3,363,969 A | 1/1968 | Brooks |
| 3,385,700 A | 5/1968 | Willems et al. |
| 3,397,984 A | 8/1968 | Williams et al. |
| 3,415,875 A | 12/1968 | Luethi et al. |
| 3,418,118 A | 12/1968 | Thommes et al. |
| 3,445,234 A | 5/1969 | Cescon et al. |
| 3,453,258 A | 7/1969 | Parmerter et al. |
| 3,453,259 A | 7/1969 | Parmerter et al. |
| 3,464,841 A | 9/1969 | Skofronick |
| 3,467,647 A | 9/1969 | Benninga |
| 3,479,185 A | 11/1969 | Chambers |
| 3,488,269 A | 1/1970 | Allen et al. |
| 3,502,476 A | 3/1970 | Kohei et al. |
| 3,503,744 A | 3/1970 | Itano et al. |
| 3,514,597 A | 5/1970 | Haes et al. |
| 3,541,142 A | 11/1970 | Cragoe, Jr. |
| 3,546,161 A | 12/1970 | Wolheim |
| 3,547,646 A | 12/1970 | Hori et al. |
| 3,549,367 A | 12/1970 | Chang et al. |
| 3,553,710 A | 1/1971 | Lloyd et al. |
| 3,563,931 A | 2/1971 | Horiguchi |
| 3,565,753 A | 2/1971 | Yurkowitz |
| 3,574,624 A | 4/1971 | Reynolds et al. |
| 3,579,533 A | 5/1971 | Yalman |
| 3,595,655 A | 7/1971 | Robinson et al. |
| 3,595,657 A | 7/1971 | Robinson et al. |
| 3,595,658 A | 7/1971 | Gerlach et al. |
| 3,595,659 A | 7/1971 | Gerlach et al. |
| 3,607,639 A | 9/1971 | Krefeld et al. |
| 3,607,693 A | 9/1971 | Heine et al. |
| 3,607,863 A | 9/1971 | Dosch |
| 3,615,562 A | 10/1971 | Harrison et al. |
| 3,617,288 A | 11/1971 | Hartman et al. |
| 3,617,335 A | 11/1971 | Kumura et al. |
| 3,619,238 A | 11/1971 | Kimura et al. |
| 3,619,239 A | 11/1971 | Osada et al. |
| 3,637,337 A | 1/1972 | Pilling |
| 3,637,581 A | 1/1972 | Horioguchi et al. |
| 3,642,472 A | 2/1972 | Mayo |
| 3,647,467 A | 3/1972 | Grubb |
| 3,652,275 A | 3/1972 | Baum et al. |
| 3,660,542 A | 5/1972 | Adachi et al. |
| 3,667,954 A | 6/1972 | Itano et al. |
| 3,668,188 A | 6/1972 | King et al. |
| 3,669,925 A | 6/1972 | King et al. |
| 3,671,096 A | 6/1972 | Mackin |
| 3,671,251 A | 6/1972 | Houle et al. |
| 3,676,690 A | 7/1972 | McMillin et al. |
| 3,678,044 A | 7/1972 | Adams |
| 3,689,565 A | 9/1972 | Hoffmann et al. |
| 3,694,241 A | 9/1972 | Guthrie et al. |
| 3,695,879 A | 10/1972 | Laming et al. |
| 3,697,280 A | 10/1972 | Strilko |
| 3,705,043 A | 12/1972 | Zablak |
| 3,707,371 A | 12/1972 | Files |
| 3,729,313 A | 4/1973 | Smith |
| 3,737,628 A | 6/1973 | Azure |
| 3,765,896 A | 10/1973 | Fox |
| 3,775,130 A | 11/1973 | Enomoto et al. |
| 3,788,849 A | 1/1974 | Taguchi et al. |
| 3,799,773 A | 3/1974 | Watarai et al. |
| 3,800,439 A | 4/1974 | Sokolski et al. |
| 3,801,329 A | 4/1974 | Sandner et al. |
| 3,817,752 A | 6/1974 | Laridon et al. |
| 3,840,338 A | 10/1974 | Zviak et al. |

| | | | | | | |
|---|---|---|---|---|---|---|
| 3,844,790 | A | 10/1974 | Chang et al. | 4,246,330 A | 1/1981 | Hara et al. |
| RE28,225 | E | 11/1974 | Heseltine et al. | 4,248,949 A | 2/1981 | Hara et al. |
| 3,870,524 | A | 3/1975 | Watanabe et al. | 4,250,096 A | 2/1981 | Kvita et al. |
| 3,873,500 | A | 3/1975 | Kato et al. | 4,251,622 A | 2/1981 | Kimoto et al. |
| 3,876,496 | A | 4/1975 | Lozano | 4,251,662 A | 2/1981 | Ozawa et al. |
| 3,887,450 | A | 6/1975 | Gilano et al. | 4,254,195 A | 3/1981 | Hara et al. |
| 3,895,949 | A | 7/1975 | Akamatsu | 4,256,493 A | 3/1981 | Yokoyama et al. |
| 3,901,779 | A | 8/1975 | Mani | 4,256,817 A | 3/1981 | Hara et al. |
| 3,904,562 | A | 9/1975 | Hopfenberg et al. | 4,258,123 A | 3/1981 | Nagashima et al. |
| 3,910,993 | A | 10/1975 | Avar et al. | 4,258,367 A | 3/1981 | Mansukhani |
| 3,914,165 | A | 10/1975 | Gaske | 4,259,432 A | 3/1981 | Kondoh et al. |
| 3,914,166 | A | 10/1975 | Rudolph et al. | 4,262,936 A | 4/1981 | Miyamoto |
| 3,915,824 | A | 10/1975 | McGinniss | 4,268,605 A | 5/1981 | Hara et al. |
| 3,919,323 | A | 11/1975 | Houlihan et al. | 4,268,667 A | 5/1981 | Anderson |
| 3,926,641 | A | 12/1975 | Rosen | 4,269,926 A | 5/1981 | Hara et al. |
| 3,928,264 | A | 12/1975 | Young, Jr. et al. | 4,270,130 A | 5/1981 | Houle et al. |
| 3,933,682 | A | 1/1976 | Bean | 4,271,252 A | 6/1981 | Hara et al. |
| RE28,789 | E | 4/1976 | Chang | 4,271,253 A | 6/1981 | Hara et al. |
| 3,952,129 | A | 4/1976 | Matsukawa et al. | 4,272,244 A | 6/1981 | Schlick |
| 3,960,685 | A | 6/1976 | Sano et al. | 4,276,211 A | 6/1981 | Singer et al. |
| 3,965,157 | A | 6/1976 | Harrison | 4,277,497 A | 7/1981 | Fromantin |
| 3,978,132 | A | 8/1976 | Houlihan et al. | 4,279,653 A | 7/1981 | Makishima et al. |
| 3,984,248 | A | 10/1976 | Sturmer | 4,279,982 A | 7/1981 | Iwasaki et al. |
| 3,988,154 | A | 10/1976 | Sturmer | 4,279,985 A | 7/1981 | Nonogaki et al. |
| 4,004,998 | A | 1/1977 | Rosen | 4,284,485 A | 8/1981 | Berner |
| 4,012,256 | A | 3/1977 | Levinos | 4,288,631 A | 9/1981 | Ching |
| 4,017,652 | A | 4/1977 | Gruber | 4,289,844 A | 9/1981 | Specht et al. |
| 4,022,674 | A | 5/1977 | Rosen | 4,290,870 A | 9/1981 | Kondoh et al. |
| 4,024,324 | A | 5/1977 | Sparks | 4,293,458 A | 10/1981 | Gruenberger et al. |
| 4,039,332 | A | 8/1977 | Kokelenberg et al. | 4,298,679 A | 11/1981 | Shinozaki et al. |
| 4,043,819 | A | 8/1977 | Baumann | 4,300,123 A | 11/1981 | McMillin et al. |
| 4,048,034 | A | 9/1977 | Martan | 4,301,223 A | 11/1981 | Nakamura et al. |
| 4,054,719 | A | 10/1977 | Cordes, III | 4,302,606 A | 11/1981 | Barabas et al. |
| 4,056,665 | A | 11/1977 | Tayler et al. | 4,306,014 A | 12/1981 | Kunikane et al. |
| 4,058,400 | A | 11/1977 | Crivello | 4,307,182 A | 12/1981 | Dalzell et al. |
| 4,067,892 | A | 1/1978 | Thorne et al. | 4,308,400 A | 12/1981 | Felder et al. |
| 4,071,424 | A | 1/1978 | Dart et al. | 4,315,807 A | 2/1982 | Felder et al. |
| 4,073,968 | A | 2/1978 | Miyamoto et al. | 4,318,705 A | 3/1982 | Nowak et al. |
| 4,077,769 | A | 3/1978 | Garcia | 4,318,791 A | 3/1982 | Felder et al. |
| 4,079,183 | A | 3/1978 | Green | 4,321,118 A | 3/1982 | Felder et al. |
| 4,085,062 | A | 4/1978 | Virgilio et al. | 4,335,054 A | 6/1982 | Blaser et al. |
| 4,090,877 | A | 5/1978 | Streeper | 4,335,055 A | 6/1982 | Blaser et al. |
| 4,100,047 | A | 7/1978 | McCarty | 4,336,323 A | 6/1982 | Winslow |
| 4,105,572 | A | 8/1978 | Gorondy | 4,343,891 A | 8/1982 | Aasen et al. |
| 4,107,733 | A | 8/1978 | Schickedanz | 4,345,011 A | 8/1982 | Drexhage |
| 4,110,112 | A | 8/1978 | Roman et al. | 4,347,111 A | 8/1982 | Gehlhaus et al. |
| 4,111,699 | A | 9/1978 | Krueger | 4,349,617 A | 9/1982 | Kawashiri et al. |
| 4,114,028 | A | 9/1978 | Baio et al. | 4,350,753 A | 9/1982 | Shelnut et al. |
| 4,126,412 | A | 11/1978 | Masson et al. | 4,351,893 A | 9/1982 | Anderson |
| 4,132,562 | A | 1/1979 | Burke, Jr. et al. | 4,356,247 A | 10/1982 | Aotani et al. |
| 4,141,807 | A | 2/1979 | Via | 4,356,255 A | 10/1982 | Tachikawa et al. |
| 4,144,156 | A | 3/1979 | Kuesters et al. | 4,357,468 A | 11/1982 | Szejtli et al. |
| 4,148,658 | A | 4/1979 | Kondoh et al. | 4,359,524 A | 11/1982 | Masuda et al. |
| 4,162,162 | A | 7/1979 | Dueber | 4,362,806 A | 12/1982 | Whitmore |
| 4,171,977 | A | 10/1979 | Hasegawa et al. | 4,367,072 A | 1/1983 | Vogtle et al. |
| 4,179,577 | A | 12/1979 | Green | 4,367,280 A | 1/1983 | Kondo et al. |
| 4,181,807 | A | 1/1980 | Green | 4,369,283 A | 1/1983 | Altschuler |
| 4,190,671 | A | 2/1980 | Vanstone et al. | 4,370,401 A | 1/1983 | Winslow et al. |
| 4,197,080 | A | 4/1980 | Mee | 4,372,582 A | 2/1983 | Geisler |
| 4,199,420 | A | 4/1980 | Photis | 4,373,017 A | 2/1983 | Masukawa et al. |
| 4,229,172 | A | 10/1980 | Baumann et al. | 4,373,020 A | 2/1983 | Winslow |
| 4,232,106 | A | 11/1980 | Iwasaki et al. | 4,374,984 A | 2/1983 | Eichler et al. |
| 4,238,492 | A | 12/1980 | Majoie | 4,376,887 A | 3/1983 | Greenaway et al. |
| 4,239,843 | A | 12/1980 | Hara et al. | 4,383,835 A | 5/1983 | Preuss et al. |
| 4,239,850 | A | 12/1980 | Kita et al. | 4,390,616 A | 6/1983 | Sato et al. |
| 4,241,155 | A | 12/1980 | Hara et al. | 4,391,867 A | 7/1983 | Derick et al. |
| 4,242,430 | A | 12/1980 | Hara et al. | 4,399,209 A | 8/1983 | Sanders et al. |
| 4,242,431 | A | 12/1980 | Hara et al. | 4,400,173 A | 8/1983 | Beavan |
| 4,245,018 | A | 1/1981 | Hara et al. | 4,401,470 A | 8/1983 | Bridger |
| 4,245,033 | A | 1/1981 | Eida et al. | 4,416,961 A | 11/1983 | Drexhage |
| 4,245,995 | A | 1/1981 | Hugl et al. | 4,421,559 A | 12/1983 | Owatari |

| | | | | | |
|---|---|---|---|---|---|
| 4,424,325 A | 1/1984 | Tsunoda et al. | 4,745,042 A | 5/1988 | Sasago et al. |
| 4,425,162 A | 1/1984 | Sugiyama | 4,746,735 A | 5/1988 | Kruper, Jr. et al. |
| 4,425,424 A | 1/1984 | Altland et al. | 4,752,341 A | 6/1988 | Rock |
| 4,426,153 A | 1/1984 | Libby et al. | 4,755,450 A | 7/1988 | Sanders et al. |
| 4,434,035 A | 2/1984 | Eichler et al. | 4,761,181 A | 8/1988 | Suzuki |
| 4,440,827 A | 4/1984 | Miyamoto et al. | 4,766,050 A | 8/1988 | Jerry |
| 4,447,521 A | 5/1984 | Tiers et al. | 4,766,055 A | 8/1988 | Kawabata et al. |
| 4,450,227 A | 5/1984 | Holmes et al. | 4,770,667 A | 9/1988 | Evans et al. |
| 4,460,676 A | 7/1984 | Fabel | 4,772,291 A | 9/1988 | Shibanai et al. |
| 4,467,112 A | 8/1984 | Matsuura et al. | 4,772,541 A | 9/1988 | Gottschalk |
| 4,475,999 A | 10/1984 | Via | 4,775,386 A | 10/1988 | Reinert et al. |
| 4,477,681 A | 10/1984 | Gehlhaus et al. | 4,786,586 A | 11/1988 | Lee et al. |
| 4,489,334 A | 12/1984 | Owatari | 4,789,382 A | 12/1988 | Neumann et al. |
| 4,495,041 A | 1/1985 | Goldstein | 4,790,565 A | 12/1988 | Steed |
| 4,496,447 A | 1/1985 | Eichler et al. | 4,800,149 A | 1/1989 | Gottschalk |
| 4,500,355 A | 2/1985 | Shimada et al. | 4,803,008 A | 2/1989 | Ciolino et al. |
| 4,508,570 A | 4/1985 | Fugii et al. | 4,808,189 A | 2/1989 | Oishi et al. |
| 4,510,392 A | 4/1985 | Litt et al. | 4,812,139 A | 3/1989 | Brodmann |
| 4,523,924 A | 6/1985 | Lacroix | 4,812,517 A | 3/1989 | West |
| 4,524,122 A | 6/1985 | Weber et al. | 4,813,970 A | 3/1989 | Kirjanov et al. |
| 4,534,838 A | 8/1985 | Lin et al. | 4,822,714 A | 4/1989 | Sanders |
| 4,548,896 A | 10/1985 | Sabongi et al. | 4,831,068 A | 5/1989 | Reinert et al. |
| 4,555,474 A | 11/1985 | Kawamura | 4,834,771 A | 5/1989 | Yamauchi et al. |
| 4,557,730 A | 12/1985 | Bennett et al. | 4,837,106 A | 6/1989 | Ishikawa et al. |
| 4,559,371 A | 12/1985 | Hiisler et al. | 4,837,331 A | 6/1989 | Yamanishi et al. |
| 4,564,560 A | 1/1986 | Tani et al. | 4,838,938 A | 6/1989 | Tomida et al. |
| 4,565,769 A | 1/1986 | Dueber et al. | 4,839,269 A | 6/1989 | Okazaki et al. |
| 4,567,171 A | 1/1986 | Mangum | 4,849,320 A | 7/1989 | Irving et al. |
| 4,571,377 A | 2/1986 | McGinniss et al. | 4,853,037 A | 8/1989 | Johnson et al. |
| 4,582,862 A | 4/1986 | Berner et al. | 4,853,398 A | 8/1989 | Carr et al. |
| 4,595,745 A | 6/1986 | Nakano et al. | 4,854,971 A | 8/1989 | Gane et al. |
| 4,604,344 A | 8/1986 | Irving et al. | 4,857,438 A | 8/1989 | Loerzer et al. |
| 4,605,442 A | 8/1986 | Kawashita et al. | 4,861,916 A | 8/1989 | Kohler et al. |
| 4,613,334 A | 9/1986 | Thomas et al. | 4,865,942 A | 9/1989 | Gottschalk et al. |
| 4,614,723 A | 9/1986 | Schmidt et al. | 4,874,391 A | 10/1989 | Reinert |
| 4,617,380 A | 10/1986 | Hinson et al. | 4,874,899 A | 10/1989 | Hoelderich et al. |
| 4,620,875 A | 11/1986 | Shimada et al. | 4,885,395 A | 12/1989 | Hoelderich |
| 4,620,876 A | 11/1986 | Fugii et al. | 4,886,774 A | 12/1989 | Doi |
| 4,622,286 A | 11/1986 | Sheets | 4,892,941 A | 1/1990 | Dolphin et al. |
| 4,631,085 A | 12/1986 | Kawanishi et al. | 4,895,880 A | 1/1990 | Gottschalk |
| 4,632,891 A | 12/1986 | Banks et al. | 4,900,581 A | 2/1990 | Stuke et al. |
| 4,632,895 A | 12/1986 | Patel et al. | 4,902,299 A | 2/1990 | Anton |
| 4,634,644 A | 1/1987 | Irving et al. | 4,902,725 A | 2/1990 | Moore |
| 4,638,340 A | 1/1987 | Iiyama et al. | 4,902,787 A | 2/1990 | Freeman |
| 4,647,310 A | 3/1987 | Shimada et al. | 4,911,732 A | 3/1990 | Neumann et al. |
| 4,655,783 A | 4/1987 | Reinert et al. | 4,911,899 A | 3/1990 | Hagiwara et al. |
| 4,663,275 A | 5/1987 | West et al. | 4,917,956 A | 4/1990 | Rohrbach |
| 4,663,641 A | 5/1987 | Iiyama et al. | 4,921,317 A | 5/1990 | Suzuki et al. |
| 4,668,533 A | 5/1987 | Miller | 4,925,770 A | 5/1990 | Ichiura et al. |
| 4,672,041 A | 6/1987 | Jain | 4,925,777 A | 5/1990 | Inoue et al. |
| 4,698,291 A | 10/1987 | Koibuchi et al. | 4,926,190 A | 5/1990 | Lavar |
| 4,701,402 A | 10/1987 | Patel et al. | 4,933,265 A | 6/1990 | Inoue et al. |
| 4,702,996 A | 10/1987 | Griffing et al. | 4,933,948 A | 6/1990 | Herkstroeter |
| 4,704,133 A | 11/1987 | Reinert et al. | 4,937,161 A | 6/1990 | Kita et al. |
| 4,707,161 A | 11/1987 | Thomas et al. | 4,942,113 A | 7/1990 | Trundle |
| 4,707,425 A | 11/1987 | Sasagawa et al. | 4,944,988 A | 7/1990 | Yasuda et al. |
| 4,707,430 A | 11/1987 | Ozawa et al. | 4,950,304 A | 8/1990 | Reinert et al. |
| 4,711,668 A | 12/1987 | Shimada et al. | 4,952,478 A | 8/1990 | Miyagawa et al. |
| 4,711,802 A | 12/1987 | Tannenbaum | 4,952,680 A | 8/1990 | Schmeidl |
| 4,713,113 A | 12/1987 | Shimada et al. | 4,954,380 A | 9/1990 | Kanome et al. |
| 4,720,450 A | 1/1988 | Ellis | 4,954,416 A | 9/1990 | Wright et al. |
| 4,721,531 A | 1/1988 | Wildeman et al. | 4,956,254 A | 9/1990 | Washizu et al. |
| 4,721,734 A | 1/1988 | Gehlhaus et al. | 4,964,871 A | 10/1990 | Reinert et al. |
| 4,724,021 A | 2/1988 | Martin et al. | 4,965,294 A | 10/1990 | Ohngemach et al. |
| 4,724,201 A | 2/1988 | Okazaki et al. | 4,966,607 A | 10/1990 | Shinoki et al. |
| 4,725,527 A | 2/1988 | Robillard | 4,966,833 A | 10/1990 | Inoue |
| 4,727,824 A | 3/1988 | Ducharme et al. | 4,968,596 A | 11/1990 | Inoue et al. |
| 4,732,615 A | 3/1988 | Kawashita et al. | 4,968,813 A | 11/1990 | Rule et al. |
| 4,737,190 A | 4/1988 | Shimada et al. | 4,985,345 A | 1/1991 | Hayakawa et al. |
| 4,737,438 A | 4/1988 | Ito et al. | 4,987,056 A | 1/1991 | Imahashi et al. |
| 4,740,451 A | 4/1988 | Kohara | 4,988,561 A | 1/1991 | Wason |

| | | | | | |
|---|---|---|---|---|---|
| 4,997,745 A | 3/1991 | Kawamura et al. | 5,180,624 A | 1/1993 | Kojima et al. |
| 5,001,330 A | 3/1991 | Koch | 5,180,652 A | 1/1993 | Yamaguchi et al. |
| 5,002,853 A | 3/1991 | Aoai et al. | 5,181,935 A | 1/1993 | Reinert et al. |
| 5,002,993 A | 3/1991 | West et al. | 5,185,236 A | 2/1993 | Shiba et al. |
| 5,003,142 A | 3/1991 | Fuller | 5,187,045 A | 2/1993 | Bonham et al. |
| 5,006,758 A | 4/1991 | Gellert et al. | 5,187,049 A | 2/1993 | Sher et al. |
| 5,013,959 A | 5/1991 | Kogelschatz | 5,190,565 A | 3/1993 | Berenbaum et al. |
| 5,017,195 A | 5/1991 | Satou et al. | 5,190,710 A | 3/1993 | Kletecka |
| 5,023,129 A | 6/1991 | Morganti et al. | 5,190,845 A | 3/1993 | Hashimoto et al. |
| 5,025,036 A | 6/1991 | Carson et al. | 5,193,854 A | 3/1993 | Borowski, Jr. et al. |
| 5,026,425 A | 6/1991 | Hindagolla et al. | 5,196,295 A | 3/1993 | Davis |
| 5,026,427 A | 6/1991 | Mitchell et al. | 5,197,991 A | 3/1993 | Rembold |
| 5,028,262 A | 7/1991 | Barlow, Jr. et al. | 5,198,330 A | 3/1993 | Martic et al. |
| 5,028,792 A | 7/1991 | Mullis | 5,202,209 A | 4/1993 | Winnik et al. |
| 5,030,243 A | 7/1991 | Reinert | 5,202,210 A | 4/1993 | Matsuoka et al. |
| 5,030,248 A | 7/1991 | Meszaros | 5,202,211 A | 4/1993 | Vercoulen |
| 5,034,526 A | 7/1991 | Bonham et al. | 5,202,212 A | 4/1993 | Shin et al. |
| 5,037,726 A | 8/1991 | Kojima et al. | 5,202,213 A | 4/1993 | Nakahara et al. |
| 5,045,435 A | 9/1991 | Adams et al. | 5,202,215 A | 4/1993 | Kanakura et al. |
| 5,045,573 A | 9/1991 | Kohler et al. | 5,202,221 A | 4/1993 | Imai et al. |
| 5,047,556 A | 9/1991 | Kohler et al. | 5,205,861 A | 4/1993 | Matrick |
| 5,049,777 A | 9/1991 | Mechtersheimer | 5,208,136 A | 5/1993 | Zanoni et al. |
| 5,053,320 A | 10/1991 | Robbillard | 5,209,814 A | 5/1993 | Felten et al. |
| 5,055,579 A | 10/1991 | Pawlowski et al. | 5,219,703 A | 6/1993 | Bugner et al. |
| 5,057,562 A | 10/1991 | Reinert | 5,221,334 A | 6/1993 | Ma et al. |
| 5,068,140 A | 11/1991 | Malhotra et al. | 5,224,197 A | 6/1993 | Zanoni et al. |
| 5,068,364 A | 11/1991 | Takagaki et al. | 5,224,987 A | 7/1993 | Matrick |
| 5,069,681 A | 12/1991 | Bouwknegt et al. | 5,226,957 A | 7/1993 | Wickramanayake et al. |
| 5,070,001 A | 12/1991 | Stahlhofen | 5,227,022 A | 7/1993 | Leonhardt et al. |
| 5,073,448 A | 12/1991 | Vieira et al. | 5,230,982 A | 7/1993 | Davis et al. |
| 5,074,885 A | 12/1991 | Reinert | 5,241,059 A | 8/1993 | Yoshinaga |
| 5,076,808 A | 12/1991 | Hahn et al. | 5,244,476 A | 9/1993 | Schultz et al. |
| 5,077,402 A | 12/1991 | Desobry et al. | 5,250,109 A | 10/1993 | Chan et al. |
| 5,085,698 A | 2/1992 | Ma et al. | 5,254,429 A | 10/1993 | Gracia et al. |
| 5,087,550 A | 2/1992 | Blum et al. | 5,256,193 A | 10/1993 | Winnik et al. |
| 5,089,050 A | 2/1992 | Vieira et al. | 5,258,274 A | 11/1993 | Helland et al. |
| 5,089,374 A | 2/1992 | Saeva | 5,261,953 A | 11/1993 | Vieira et al. |
| 5,096,456 A | 3/1992 | Reinert et al. | 5,262,276 A | 11/1993 | Kawamura |
| 5,096,489 A | 3/1992 | Laver | 5,268,027 A | 12/1993 | Chan et al. |
| 5,096,781 A | 3/1992 | Vieira et al. | 5,270,078 A | 12/1993 | Walker et al. |
| 5,098,477 A | 3/1992 | Vieira et al. | 5,271,764 A | 12/1993 | Winnik et al. |
| 5,098,793 A | 3/1992 | Rohrbach et al. | 5,271,765 A | 12/1993 | Ma |
| 5,098,806 A | 3/1992 | Robillard | 5,272,201 A | 12/1993 | Ma et al. |
| 5,106,723 A | 4/1992 | West et al. | 5,275,646 A | 1/1994 | Marshall et al. |
| 5,108,505 A | 4/1992 | Moffat | 5,279,652 A | 1/1994 | Kaufmann et al. |
| 5,108,874 A | 4/1992 | Griffing et al. | 5,282,894 A | 2/1994 | Albert et al. |
| 5,110,706 A | 5/1992 | Yumoto et al. | 5,284,734 A | 2/1994 | Blum et al. |
| 5,110,709 A | 5/1992 | Aoai et al. | 5,286,286 A | 2/1994 | Winnik et al. |
| 5,114,832 A | 5/1992 | Zertani et al. | 5,286,288 A | 2/1994 | Tobias et al. |
| 5,124,723 A | 6/1992 | Laver | 5,294,528 A | 3/1994 | Furutachi |
| 5,130,227 A | 7/1992 | Wade et al. | 5,296,275 A | 3/1994 | Goman et al. |
| 5,133,803 A | 7/1992 | Moffatt | 5,296,556 A | 3/1994 | Frihart |
| 5,135,940 A | 8/1992 | Belander et al. | 5,298,030 A | 3/1994 | Burdeska et al. |
| 5,139,572 A | 8/1992 | Kawashima | 5,300,403 A | 4/1994 | Angelopolus et al. |
| 5,139,687 A | 8/1992 | Borgher, Sr. et al. | 5,300,654 A | 4/1994 | Nakajima et al. |
| 5,141,556 A | 8/1992 | Matrick | 5,302,195 A | 4/1994 | Helbrecht |
| 5,141,797 A | 8/1992 | Wheeler | 5,302,197 A | 4/1994 | Wickramanayake et al. |
| 5,144,964 A | 9/1992 | Demian | 5,310,778 A | 5/1994 | Shor et al. |
| 5,147,901 A | 9/1992 | Rutsch et al. | 5,312,713 A | 5/1994 | Yokoyama et al. |
| 5,153,104 A | 10/1992 | Rossman et al. | 5,312,721 A | 5/1994 | Gesign |
| 5,153,105 A | 10/1992 | Sher et al. | 5,324,349 A | 6/1994 | Sano et al. |
| 5,153,166 A | 10/1992 | Jain et al. | 5,328,504 A | 7/1994 | Ohnishi |
| 5,160,346 A | 11/1992 | Fuso et al. | 5,330,860 A | 7/1994 | Grot et al. |
| 5,160,372 A | 11/1992 | Matrick | 5,334,455 A | 8/1994 | Noren et al. |
| 5,166,041 A | 11/1992 | Murofushi et al. | 5,338,319 A | 8/1994 | Kaschig et al. |
| 5,169,436 A | 12/1992 | Matrick | 5,340,631 A | 8/1994 | Matsuzawa et al. |
| 5,169,438 A | 12/1992 | Matrick | 5,340,854 A | 8/1994 | Martic et al. |
| 5,173,112 A | 12/1992 | Matrick et al. | 5,344,483 A | 9/1994 | Hinton |
| 5,176,984 A | 1/1993 | Hipps, Sr. et al. | 5,356,464 A | 10/1994 | Hickman et al. |
| 5,178,420 A | 1/1993 | Shelby | 5,362,592 A | 11/1994 | Murofushi et al. |
| 5,180,425 A | 1/1993 | Matrick et al. | 5,362,916 A | 11/1994 | Edwards et al. |

| | | |
|---|---|---|
| 5,368,689 A | 11/1994 | Agnemo |
| 5,372,387 A | 12/1994 | Wajda |
| 5,372,917 A | 12/1994 | Tsuchida et al. |
| 5,374,335 A | 12/1994 | Lindgren et al. |
| 5,376,503 A | 12/1994 | Audett et al. |
| 5,383,961 A | 1/1995 | Bauer et al. |
| 5,384,186 A | 1/1995 | Trinh |
| 5,393,580 A | 2/1995 | Ma et al. |
| 5,401,303 A | 3/1995 | Stoffel et al. |
| 5,401,562 A | 3/1995 | Akao |
| 5,407,969 A | 4/1995 | Kleiner et al. |
| 5,415,686 A | 5/1995 | Kurabayashi et al. |
| 5,415,976 A | 5/1995 | Ali |
| 5,424,407 A | 6/1995 | Tanaka et al. |
| 5,425,978 A | 6/1995 | Berneth et al. |
| 5,426,164 A | 6/1995 | Babb et al. |
| 5,427,415 A | 6/1995 | Chang |
| 5,429,628 A | 7/1995 | Trinh et al. |
| 5,431,720 A | 7/1995 | Nagai et al. |
| 5,432,274 A | 7/1995 | Luong et al. |
| 5,445,651 A | 8/1995 | Thoen et al. |
| 5,445,842 A | 8/1995 | Tanaka et al. |
| 5,455,074 A | 10/1995 | Nohr et al. |
| 5,455,143 A | 10/1995 | Ali |
| 5,459,014 A | 10/1995 | Nishijima et al. |
| 5,464,472 A | 11/1995 | Horn et al. |
| 5,466,283 A | 11/1995 | Kondo et al. |
| 5,474,691 A | 12/1995 | Severns |
| 5,475,080 A | 12/1995 | Gruber et al. |
| 5,476,540 A | 12/1995 | Shields et al. |
| 5,479,949 A | 1/1996 | Battard et al. |
| 5,489,503 A | 2/1996 | Toan |
| 5,498,345 A | 3/1996 | Jollenbeck et al. |
| 5,501,774 A | 3/1996 | Burke |
| 5,501,902 A | 3/1996 | Kronzer |
| 5,503,664 A | 4/1996 | Sano et al. |
| 5,509,957 A | 4/1996 | Toan et al. |
| 5,531,821 A | 7/1996 | Wu |
| 5,532,112 A | 7/1996 | Kohler et al. |
| 5,541,633 A | 7/1996 | Winnik et al. |
| 5,543,459 A | 8/1996 | Hartmann et al. |
| 5,569,529 A | 10/1996 | Becker et al. |
| 5,571,313 A | 11/1996 | Mafune et al. |
| 5,575,891 A | 11/1996 | Trokhan et al. |
| 5,580,369 A | 12/1996 | Belding et al. |
| 5,591,489 A | 1/1997 | Dragner et al. |
| 5,597,405 A | 1/1997 | Grigoryan et al. |
| 5,607,803 A | 3/1997 | Murofushi et al. |
| 5,616,443 A | 4/1997 | Nohr et al. |
| 5,635,297 A | 6/1997 | Ogawa et al. |
| 5,643,356 A | 7/1997 | Nohr et al. |
| 5,643,631 A | 7/1997 | Donigian et al. |
| 5,643,701 A | 7/1997 | Nohr et al. |
| 5,645,964 A | 7/1997 | Nohr et al. |
| 5,672,392 A | 9/1997 | De Clercq et al. |
| 5,681,380 A | 10/1997 | Nohr et al. |
| 5,683,843 A | 11/1997 | Nohr et al. |
| 5,685,754 A | 11/1997 | Nohr et al. |
| 5,686,503 A | 11/1997 | Nohr et al. |
| 5,700,582 A | 12/1997 | Sargeant et al. |
| 5,700,850 A | 12/1997 | Nohr et al. |
| 5,705,247 A | 1/1998 | Arai et al. |
| 5,709,955 A | 1/1998 | Nohr et al. |
| 5,709,976 A | 1/1998 | Malhotra |
| 5,721,287 A | 2/1998 | Nohr et al. |
| 5,733,693 A | 3/1998 | Nohr et al. |
| 5,738,932 A | 4/1998 | Kondo et al. |
| 5,739,175 A | 4/1998 | Nohr et al. |
| 5,747,550 A | 5/1998 | Nohr et al. |
| 5,773,182 A | 6/1998 | Nohr et al. |
| 5,782,963 A | 7/1998 | Nohr et al. |
| 5,786,132 A | 7/1998 | Nohr et al. |
| 5,798,015 A | 8/1998 | Nohr et al. |
| 5,811,199 A | 9/1998 | MacDonald et al. |
| 5,837,429 A | 11/1998 | Nohr et al. |
| 5,849,411 A | 12/1998 | Nohr et al. |
| 5,855,655 A | 1/1999 | Nohr et al. |
| 5,856,515 A | 1/1999 | Therien et al. |
| 5,865,471 A | 2/1999 | Nohr et al. |
| 5,883,161 A | 3/1999 | Wood et al. |
| 5,885,337 A | 3/1999 | Nohr et al. |
| 5,891,229 A | 4/1999 | Nohr et al. |
| 5,911,855 A | 6/1999 | Dransmann et al. |
| 6,022,906 A | 2/2000 | Ohwa et al. |
| 6,099,628 A * | 8/2000 | Nohr et al. .............. 106/31.49 |
| 6,168,655 B1 * | 1/2001 | Nohr et al. .............. 106/31.58 |

FOREIGN PATENT DOCUMENTS

| | | |
|---|---|---|
| CA | 458808 | 12/1936 |
| CA | 460268 | 10/1949 |
| CA | 461082 | 11/1949 |
| CA | 463021 | 2/1950 |
| CA | 463022 | 2/1950 |
| CA | 465495 | 5/1950 |
| CA | 465496 | 5/1950 |
| CA | 465499 | 5/1950 |
| CA | 483214 | 5/1952 |
| CA | 517364 | 10/1955 |
| CA | 537687 | 3/1957 |
| CA | 552565 | 2/1958 |
| CA | 571792 | 3/1959 |
| CA | 779239 | 2/1968 |
| CA | 930103 | 7/1973 |
| CA | 2053094 | 4/1992 |
| CH | 603767 | 8/1978 |
| CH | 197808 | 5/1988 |
| CS | 94118 | 5/1958 |
| DE | 1047787 | 12/1957 |
| DE | 1022801 | 1/1958 |
| DE | 1039835 | 9/1958 |
| DE | 1040562 | 10/1958 |
| DE | 1045414 | 12/1958 |
| DE | 1047013 | 12/1958 |
| DE | 1132540 | 7/1962 |
| DE | 1154069 | 9/1963 |
| DE | 1240811 | 5/1967 |
| DE | 2202497 | 8/1972 |
| DE | 2432563 | 2/1975 |
| DE | 2437380 | 2/1975 |
| DE | 2444520 | 3/1975 |
| DE | 2416259 | 10/1975 |
| DE | 2714978 | 10/1977 |
| DE | 2722264 | 11/1978 |
| DE | 158237 | 1/1983 |
| DE | 3126433 | 1/1983 |
| DE | 3415033 | 10/1984 |
| DE | 271512 | 9/1989 |
| DE | 3921600 | 1/1990 |
| DE | 3833437 | 4/1990 |
| DE | 3833438 | 4/1990 |
| DE | 004036328 | 7/1991 |
| DE | 4132288 | 4/1992 |
| DE | 4126461 | 2/1993 |
| EP | 0003884 | 9/1979 |
| EP | 0029284 | 5/1981 |
| EP | 0127574 | 12/1984 |
| EP | 0202803 | 11/1986 |
| EP | 0 209 831 | 1/1987 |
| EP | 0223587 | 5/1987 |
| EP | 0262533 | 4/1988 |
| EP | 0280458 | 8/1988 |
| EP | 0 303 803 | 2/1989 |

| | | | | | |
|---|---|---|---|---|---|
| EP | 0308274 | 3/1989 | JP | 59-219270 | 4/1985 |
| EP | 0351615 | 1/1990 | JP | 60-192729 | 10/1985 |
| EP | 0371304 | 6/1990 | JP | 60239739 | 11/1985 |
| EP | 0373662 | 6/1990 | JP | 60239740 | 11/1985 |
| EP | 0375160 | 6/1990 | JP | 60239741 | 11/1985 |
| EP | 0390439 | 10/1990 | JP | 60239743 | 11/1985 |
| EP | 0433201 | 6/1991 | JP | 61-288 | 1/1986 |
| EP | 0458140 A1 | 10/1991 | JP | 613781 | 1/1986 |
| EP | 0458140 | 11/1991 | JP | 61-14994 | 1/1986 |
| EP | 0468465 | 1/1992 | JP | 61-14995 | 1/1986 |
| EP | 0 469 595 | 2/1992 | JP | 61-21184 | 1/1986 |
| EP | 0 475 075 | 3/1992 | JP | 61-25885 | 2/1986 |
| EP | 0542286 | 5/1993 | JP | 61-30592 | 2/1986 |
| EP | 000571190 | 11/1993 | JP | 61-40366 | 2/1986 |
| EP | 0 605 840 | 7/1994 | JP | 61-77846 | 4/1986 |
| EP | 0608433 | 8/1994 | JP | 61-128973 | 6/1986 |
| EP | 0609159 | 8/1994 | JP | 61-97025 | 9/1986 |
| EP | 0 635 380 | 1/1995 | JP | 61-222789 | 10/1986 |
| EP | 0639664 | 2/1995 | JP | 61-247703 | 11/1986 |
| EP | 0658607 | 6/1995 | JP | 61-285403 | 12/1986 |
| EP | 0 673 779 | 9/1995 | JP | 627703 | 1/1987 |
| EP | 0694594 | 1/1996 | JP | 62-97881 | 5/1987 |
| EP | 0 716 929 | 6/1996 | JP | 62-100557 | 5/1987 |
| EP | 0 737 592 | 10/1996 | JP | 62127281 | 6/1987 |
| EP | 0755984 | 1/1997 | JP | 63-43959 | 2/1988 |
| EP | 0 805 152 | 11/1997 | JP | 63-48370 | 3/1988 |
| EP | 0 861 880 | 9/1998 | JP | 6395439 | 4/1988 |
| EP | 0878482 | 11/1998 | JP | 6395440 | 4/1988 |
| FR | 2245010 | 4/1975 | JP | 6395445 | 4/1988 |
| FR | 2383157 | 10/1978 | JP | 6395446 | 4/1988 |
| GB | 275245 | 10/1928 | JP | 6395447 | 4/1988 |
| GB | 349339 | 5/1931 | JP | 6395448 | 4/1988 |
| GB | 355686 | 8/1931 | JP | 6395449 | 4/1988 |
| GB | 399753 | 10/1933 | JP | 6395450 | 4/1988 |
| GB | 441085 | 1/1936 | JP | 63151946 | 6/1988 |
| GB | 463515 | 4/1937 | JP | 63-164953 | 7/1988 |
| GB | 492711 | 9/1938 | JP | 63-165498 | 7/1988 |
| GB | 518612 | 3/1940 | JP | 63-223077 | 9/1988 |
| GB | 539912 | 9/1941 | JP | 63-223078 | 9/1988 |
| GB | 626727 | 7/1947 | JP | 63-243101 | 10/1988 |
| GB | 600451 | 4/1948 | JP | 63-199781 | 12/1988 |
| GB | 616362 | 1/1949 | JP | 64-15049 | 1/1989 |
| GB | 618616 | 2/1949 | JP | 6429337 | 1/1989 |
| GB | 779389 | 7/1957 | JP | 64-40948 | 2/1989 |
| GB | 1150987 | 5/1969 | JP | 89014948 | 3/1989 |
| GB | 1372884 | 11/1974 | JP | 1-128063 | 5/1989 |
| GB | 2146357 | 4/1985 | JP | 1146974 | 6/1989 |
| IT | 662500 | 4/1964 | JP | 01210477 | 8/1989 |
| JP | 424756 | 1/1967 | JP | 1288854 | 11/1989 |
| JP | 4315663 | 7/1968 | JP | 2-58573 | 2/1990 |
| JP | 4726653 | 7/1972 | JP | 292957 | 4/1990 |
| JP | 4745409 | 11/1972 | JP | 2179642 | 7/1990 |
| JP | 49-8909 | 2/1974 | JP | 2282261 | 11/1990 |
| JP | 5065592 | 6/1975 | JP | 3-134072 | 6/1991 |
| JP | 51-17802 | 2/1976 | JP | 03163566 | 7/1991 |
| JP | 53-104321 | 9/1978 | JP | 3-170415 | 7/1991 |
| JP | 55-62059 | 5/1980 | JP | 3-206439 | 9/1991 |
| JP | 55-90506 | 7/1980 | JP | 3-258867 | 11/1991 |
| JP | 56-8134 | 1/1981 | JP | 3-203694 | 12/1991 |
| JP | 0014233 | 2/1981 | JP | 3284668 | 12/1991 |
| JP | 5614569 | 2/1981 | JP | 4023884 | 1/1992 |
| JP | 56-24472 | 3/1981 | JP | 4023885 | 1/1992 |
| JP | 56-36556 | 4/1981 | JP | 4-45174 | 2/1992 |
| JP | 5761055 | 4/1982 | JP | 4100801 | 4/1992 |
| JP | 57128283 | 8/1982 | JP | 4-136075 | 5/1992 |
| JP | 57171775 | 10/1982 | JP | 04356087 | 12/1992 |
| JP | 58-124452 | 7/1983 | JP | 543806 | 2/1993 |
| JP | 58-125770 | 7/1983 | JP | 561220 | 3/1993 |
| JP | 58-222164 | 12/1983 | JP | 5080506 | 4/1993 |
| JP | 5989360 | 5/1984 | JP | 05119506 | 5/1993 |
| JP | 29219270 | 12/1984 | JP | 5134447 | 5/1993 |

| | | |
|---|---|---|
| JP | 5-140498 | 6/1993 |
| JP | 2-219869 | 9/1993 |
| JP | 5263067 | 10/1993 |
| JP | 680915 | 3/1994 |
| JP | 6116555 | 4/1994 |
| JP | 6116556 | 4/1994 |
| JP | 6116557 | 4/1994 |
| JP | 6-175584 | 6/1994 |
| JP | 6214339 | 8/1994 |
| JP | 6256494 | 9/1994 |
| JP | 6256633 | 9/1994 |
| NL | 7113828 | 4/1972 |
| RU | 1772118 | 10/1992 |
| SU | 1310767 | 5/1987 |
| WO | 92/11295 | 7/1992 |
| WO | 93/06597 | 4/1993 |
| WO | 94/01503 | 1/1994 |
| WO | 94/22500 | 10/1994 |
| WO | 94/22501 | 10/1994 |
| WO | 95/04955 | 2/1995 |
| WO | 95/28285 | 10/1995 |
| WO | 96/00740 | 1/1996 |
| WO | 96/19502 | 6/1996 |
| WO | 96/22335 | 7/1996 |
| WO | 96/24636 | 8/1996 |
| WO | 97/20000 | 6/1997 |
| WO | 97/35933 | 10/1997 |
| WO | 98/23695 | 6/1998 |
| WO | 99/36476 | 7/1999 |

OTHER PUBLICATIONS

Kubat et al. "Photophysical properties of metal complexes of meso–tetrakis (40sulphonatophenyl) porphyrin," *J. Photochem. and Photobiol.* 96 93–97, no month available.
Derwent World Patents Index EP 659039 (Canon KK) Jun. 21, 1995. abstract 1995.
Derwent World Patents Index JP 7061114 (Dainippon Printing Co. Ltd.) Mar. 7, 1995. abstract 1995.
Abstract for WO 95/00343—A1 *Textiles: Paper: Cellulose* p. 7 1995, no month available.
Maki, Y. et al. "A novel heterocyclic N–oxide, pyrimidol[5,4–g]pteridinetetrone 5–oxide, with multifunctional photo-oxidative properties" *Chemical Abstracts* 122 925 [no 122:31350 F] 1995, no month available.
Patent Abstracts of Japan JP 06200204 (Brother Ind Ltd), Jul. 19, 1994 1994.
Abstract of patent, JP 6–80915 (Canon Inc.), Mar. 22, 1994, 1994.
Abstract of patent, JP 06–43573 (Iku Meji) (Feb. 18, 1994), 1994.
Pitchumani, K. "Modification of chemical reactivity upon cyclodextrin encapsulation" *Chemical Abstracts* 121 982 [no. 121:13362 4v] 1994, no month available.
Wijesekera, T.P., et al. Synthetic Aspects of Pophyrin and Metalloporphyrin Chemistry *Metalloporpyrins in Catalytic Oxidations* pp. 202–203, 206–207, 1994, no month available.
Derwent Publications Ltd., London, JP 05297627 (Fujitsu Ltd.), Nov. 12, 1993. (Abstract) 1993.
Patent Abstracts of Japan, JP 5241369 (Bando Chem Ind Ltd et al.), Sep. 21, 1993. (Abstract) 1993.
Derwent Publications Ltd., London, JP 05232738 (Yamazaki, T.), Sep. 10, 1993. (Abstract) 1993.
Derwent Publications Ltd., London, EP 000559310 (Zeneca Ltd.), Sep. 8, 1993. (Abstract) 1993.
Derwent Publications Ltd., London, J,A, 5–230410 (Seiko Epson Corp), Sep. 7, 1993. (Abstract) 1993.
Derwent Publications Ltd., London, JP 5–230407 (Mitsubishi Kasei Corp), Sep. 7, 1993. (Abstract) 1993.
Abstract Of Patent, JP 405230410 (Seiko Epson Corp.), Sep. 7, 1993. (Abstract) 1993.
Abstract Of Patent, JP 405230407 (Mitsubishi Kasei Corp.), Sep. 7, 1993. (Abstract) 1993.
Patent Abstracts of Japan, JP 5197198 (Bando Chem Ind Ltd et al.), Aug. 6, 1993. (Abstract) 1993.
Database WPI–Derwent Publications Ltd., London, J,A 5197069 (Bando Chem), Aug. 6, 1993. (Abstract) 1993.
Abstract of patent, JP 5–195450 (Nitto Boseki Co. Ltd), Aug. 3, 1993. 1993.
Derwent World JP 5186725 (Seiko Epson Corp.), Patents Index Jul. 27, 1993. abstract 1993.
Derwent World JP 5186725 (Seiko Epson Corp.), Patents Index Jul. 27, 1993. abstract 1993.
Patent Abstracts of Japan, JP 5181308 (Bando Chem Ind Ltd et al.), Jul. 23, 1993. (Abstract).
Patent Abstracts of Japan, JP 5181310 (Bando Chem Ind Ltd et al.), Jul. 23, 1993. (Abstract) 1993.
Derwent Publications Ltd., London, JP 5–132638 (Mitsubishi Kasei Corp), May 28, 1993. (Abstract) 1993.
Abstract Of Patent, JP 405132638 (Mitsubishi Kasei Corp.), May 28, 1993. (Abstract) 1993.
Derwent Publications Ltd., London, JP 5–125318 (Mitsubishi Kasei Corp), May 21, 1993. (Abstract).
Abstract Of Patent, JP 405125318 Mitsubishi Kasei Corp.), May 21, 1993. (Abstract) 1993.
Abstract of patent, JP 05–117200 (Hidefumi Hirai et al.) May 14, 1993) 1993.
Derwent World Patents Index, JP 5117105 (Mitsui Toatsu Chem Inc.) May 14, 1993. 1993.
Derwent Publications Ltd., London, JP 05061246 (Ricoh KK), Mar. 12, 1993. (Abstract) 1993.
Husain, N. et al. "Cyclodextrins as mobile–phase additives in reversed–phase HPLC" *American Laboratory* 82 80–87 1993, no month available.
Hamilton, D.P. "Tired of Shreding? New Ricoh Method Tries Different Tack" *Wall Street Journal* B2 1993, no month available.
"Cyclodextrins: A Breakthrough for Molecular Encapsulation" *American Maize Products Co.* (*AMAIZO*) 1993, no month available.
Duxbury "The Photochemistry and Photophysics of Triphenylmethane Dyes in Solid Liquid Media" *Chemical Review* 93 381–433 1993, no month available.
Abstract of patent, JP 04–351603 (Dec. 7, 1992) 1992.
Abstract of patent, JP 04–351602 1992, no month available.
Derwent Publications Ltd., London, JP 404314769 (Citizen Watch Co. Ltd.), Nov. 5, 1992. (Abstract) 1992.
Abstract of patent, JP 04315739 1992, no month available.
Derwent Publications Ltd., London, JP 04300395 (Funai Denki KK), Oct. 23, 1992. (Abstract) 1992.
Derwent Publications Ltd., London, JP 404213374 (Mitsubishi Kasei Corp), Aug. 4, 1992. (Abstract) 1992.
Abstract of patent, JP 04–210228 1992, no month available.
Abstract Of Patent, JP 404202571 (Canon Inc.), Jul. 23, 1992. (Abstract) 1992.
Abstract Of Patent, JP 404202271 (Mitsubishi Kasei Corp.), Jul. 23, 1992. (Abstract) 1992.
Derwent WPI, JP 4–197657 (Toshiba KK) Jul. 17, 1992, abstract. 1992.
Derwent Publications Ltd., London, JP 4–198877 (Seiko Epson Corp), Jul. 8, 1992. (Abstract) 1992.

Derwent Publications Ltd., London, JP 404189876 (Seiko Epson Corp), Jul. 8, 1992. (Abstract) 1992.
Abstract Of Patent, JP 404189877 (Seiko Epson Corp.), Jul. 8, 1992. (Abstract) 1992.
Derwent Publications Ltd., London, J,A, 4–170479 (Seiko Epson Corp), Jul. 18, 1992. (Abstract) 1992.
Abstract of patent, JP 04–81402 1992, no month available.
Abstract of patent, JP 04–81401 1992, no month available.
Kogelschatz "Silent–discharge driven excimer UV sources and their applications" *Applied Surface Science* 410–423 1992, no month available.
Patent Abstracts of Japan JP 03295653 (Matsushita Electric Works Ltd.), Dec. 26, 1991 1991.
Derwent Publications, Ltd., London, JP 403269167 (Japan Wool Textile KK), Nov. 29, 1991 (Abstract) 1991.
Derwent Publications Ltd., London, JO 3247676 (Canon KK), Nov. 5, 1991 (Abstract).
Tang, F. Synthesis and Properties of 5, 10, 15, 20–tetrakis (4–=methoxyl–3–sulfophenyl) porphine *Chem. Abstracts* 115(17) 1991, no month available.
Abstract of patent, JP 03–220384 1991, no month available.
Patent Abstracts of Japan, JP 03184896 (Dainippon Printing Co Ltd.) Aug. 12, 1991. 1991.
Derwent Publications Ltd., London, JP 3167270 (Mitsubishi Kasei Corp), Jul. 19, 1991. (Abstract) 1991.
Derwent World Patents Index EP 435536 (Canon KK) Jul. 3, 1991. abstract 1991, no month available.
Derwent Publications Ltd., London, JO 3093870 (Dainippon Ink Chem KK.), Apr. 18, 1991 (Abstract) 1991.
Abstract of patent, JP 06369890 1991, no month available.
Kogelschatz, U. "New Excimer UV Sources for Industrial Applications" *ABB Review* 391 1–10 1991, no month available.
Abstract of patent, JP 03–41165 1991, no month available.
"Coloring/Decoloring Agent for Tonor Use Developed" *Japan Chemical Week* 1991, no month available.
Braithwaite, M., et al. "Formulation" *Chemistry & Technology of UV & EB Formulation for Coatings, Inks & Paints* IV 11–12 1991, no month available.
*Scientific Polymer Products, Inc. Brochure* 24–31 1991.
Dietliker, K. "Photoiniators for Free Radical and Catioinic Polymerisation" *Chem & Tech of UV & EB Formulation for Coatings, Inks & Paints* III 61, 63, 229–232, 280, 405, 1991, no month available.
Esrom et al. "Large area Photochemical Dry Etching of Polymers iwth Incoherent Excimer UV Radiation" *MRS Materials Research Society* 1–7 1991, no month available.
Esrom et al. Excimer Laser–Induced Decomposition of Aluminum Nitride *Materials Research Society Fall Meeting* 1–6 1991, no month available.
Esrom et al. "Metal deposition with a windowless VUV excimer source" *Applied Surface Science* 1–5 1991, no month available.
Esrom "Excimer Laser–Induced Surface Activation of Aln for Electroless Metal Deposition" *Mat. Res. Sco.1Symp. Proc.* 204 457–465 1991, no month available.
Zhang et al. "UV–induced decomposition of adsorbed Cu–acetylacetonate films at room temperature for electroless metal plating" *Applied Surface Science* 1–6 1991, no month available.
"Coloring/Decoloring Agent for Tonor Use Developed" *Japan Chemical Week* 1991, no month available.
"German company develops reusable paper" *Pulp & Paper* 1991, no month available.

Abstract of patent, JP 02289652 1990, no month available.
Ohashi et al. "Molecular Mechanics Studies on Inclusion Compounds of Cyanine Dye Monomers and Dimers in Cyclodextrin Cavities," *J. Am. Chem. Soc.* 112 5824–5830 1990, no month available.
Kogelschatz et al. "New Incoherent Ultraviolet Excimer Sources for Photolytic Material Deposition," *Laser Und Optoelektronik* 1990, no month available.
Patent Abstracts of Japan, JP 02141287 (Dainippon Printing Co Ltd.) May 30, 1990. 1990.
Abstract of Patent, JP 0297957, (Fuji Xerox Co., Ltd.) 1990, no month available.
Derwent Publications Ltd., London, JP 2091166 (Canon KK), Mar. 30, 1990. (Abstract) 1990.
Zhang, Zhoupent Synthesis of 7 meso–tetrasubstituted porphyrins *Chem. Abstracts* 113(9) 1990, no month available.
Esrom et al. "Metal Deposition with Incoherent Excimer Radiation" *Mat. Res. Soc. Symp. Proc.* 158 189–198 1990, no month available.
Esrom "UV Excimer Laser–Induced Deposition of Palladium from palladiym Acetate Films" *Mat. Res. Soc. Symp. Proc.* 158 109–117 1990, no month available.
Kogelschatz, U. "Silent Discharges for the Generation of ultraviolet and vacuum ultraviolet excimer radiation" *Pure & Applied Chem.* 62 1667–74 1990, no month available.
Esrom et al. "Investigation of the mechanism of the UV–induced palladium depositions processf from thin solid palladium acetate films" *Applied Surface Science* 46 158–162 1990, no month available.
Zhang et al. "VUV synchrotron radiation processing of thin palladium acetate spin–on films for metallic surface patterning" *Applied Surface Science* 46 153–157 1990, no month available.
Brennan et al. "Stereoelectronic effects in ring closure reactions: the 2'–hydroxychalcone—flavanone equilibrium, and related systems," *Canadian J. Chem.* 68 (10) pp. 1780–1785 1990, no month available.
Abstract of patent, JP 01–299083 1989, no month available.
Derwent Publications Ltd., London, J,0, 1182379 (Canon KK), Jul. 20, 1989. (Abstract) 1989.
Derwent Publications Ltd., London, JO 1011171 (Mitsubishi Chem Ind. KK.), Jan. 13, 1989 (Abstract) 1989.
Gruber, R.J., et al. "Xerographic Materials" *Encyclopedia of Polymer Science and Engineering* 17 918–943 1989, no month available.
Pappas, S.P. "Photocrosslinking" *Comph. Pol. Sci.* 6 135–148 1989, no month available.
Pappas, S.P. "Photoinitiated Polymerization" *Comph. Pol. Sci.* 4 337–355 1989, no month available.
Kirilenko, G.V. et al. "An analog of the vesicular process with amplitude modulation of the incident light beam" *Chemical Abstracts* 111 569 [no. 111:12363 3b] 1989, no month available.
Esrom et al. "UV excimer laser–induced pre–nucleation of surfaces followed by electroless metallization" *Chemtronics* 4 216–223 1989, no month available.
Esrom et al. "VUV light–induced deposition of palladium using an incoherent Xe2* excimer source" *Chemtronics* 4 1989, no month available.
Esrom et al. "UV Light–Induced Deposition of Copper Films" C5–179–C5–725 1989, no month available.
Falbe et al. *Rompp Chemie Lexikon* 9 270 1989, no month available.

Allen, Norman S. *Photopolymerisation and Photoimaging Science and Technology* pp. 188–199; 210–239 1989, no month available.

Lindsey, J.S. et al. Investigation of the Synthesis of Ortho–Substituted Tetraphenylporphyrins *J. Org. Chem.* 54 pp. 828–836 1989, no month available.

Patent Abstracts of Japan, JP 63297477 (Fuji Photo Film Co. Ltd.) Dec. 5, 1988, abstract 1988.

Derwent Publications, Ltd., London, SU 1423656 (Kherson Ind Inst), Sep. 15, 1988 (Abstract 1988.

Derwent Publications, Ltd., London, EP 0280653 (Ciba GeigAG), Aug. 31, 1988 (Abstract) 1988.

Abstract of patent, JP 63–190815 1988, no month available.

Patent Abstracts of Japan, JP 63179985 (Tomoegawa Paper Co. Ltd.), Jul. 23, 1988, 1988.

Derwent World Patents Index, JP 63179977 (Tomoegawa Paper Mfg Co Ltd), Jul. 23, 1988 1988.

Furcone, S.Y. et al. "Spin–on B14Sr3Ca3Ca3Cu4O16+x superconducting thin films from citrate precursors," *Appl. Phys. Lett.* 52(22) 2180–2182 1988, no month available.

Abstract of patent, JP 63–144329 1988, no month available.
Abstract of patent, JP 63–130164 1988, no month available.

Derwent Publications, Ltd., London, J6 3112770 (Toray Ind Inc), May 17, 1988 (Abstract) 1988.

Derwent Publications, Ltd., London, J6 3108074 (Konishiroku Photo KK), May 12, 1988 (Abstract) 1988.

Derwent Publications, Ltd., London,J6 3108073 (Konishiroku Photo KK), May 12, 1988 (Abstract) 1988.

Abstract of patent, JP 61–77846 1988, no month available.
Abstract of patent, JP 63–73241 1988, no month available.

Patent Abstracts of Japan JP 63062738 (Seiko Epson Corp), Mar. 19, 1988 1988.

Abstract of patent, JP 63–47762, 1988, no month available.
Abstract of patent, JP 63–47763, 1988, no month available.
Abstract of patent, JP 63–47764, 1988, no month available.
Abstract of patent, JP 63–47765 1988, no month available.

Eliasson, B., et al., "UV Excimer Radiation from Dielectric–Barrier Discharges" *Applied Physics B* 46 299–303 1988, no month available.

Eliasson et al. "New Trends in High Intensity UV Generation" *EPA Newlsetter* (32) 29–40 1988, no month available.

Cotton, F.A. "Oxygen: Group Via(16)" *Advanced Inorganic Chemistry* 5th ed. 473–474 1988, no month available.

Derwent Publications, Ltd., London, J6 2270665 (Konishiroku Photo KK), Nov. 25, 1987 (Abstrac) 1987.

Abstract of patent, JP 62–215261 1987, no month available.

Derwent World Patents Index JP 62064874 (Dainichiseika Color & Chem Mfg.), Mar. 23, 1987. abstract 1987.

Derwent World Patents Index JP 62064874 (Dainichisieka Color & Chem Mfg.), Mar. 23, 1987. abstract 1987.

Database WPI, Derwent Publications Ltd., London, JP 62032082 (Mitsubishi Denki KK), Feb. 21, 1987, (Abstract) 1987.

Abstract of patent, JP 62–32082 1987, no month available.

Derwent Publications Ltd., London, J6 2007772 (Alps Electric KK.), Jan. 14, 1987 (Abstract) 1987.

Gross et al. "Laser direct–write metallization in thin palladium acetate films" *J. App. Phys.* 61 (4) 1628–1632 1987, no month available.

Al–Ismail et al. "Some experimental results on thin polypropylene films loaded with finely–dispersed copper" *Journal of Materials Science* 415–418 1987, no month available.

Baufay et al. "Optical self–regulation during laser–induced oxidation of copper" *J. Appl. Phys* 61 4640–4651 (9) 1987, no month available.

Al–Ismail et al. "Some experimental results on thin polypropylene films loaded with finely–dispersed copper" *Journal of Materials Science* 415–418 1987, no month available.

Gross et al. "Laser direct–write metallization in thin palladium acetate films" *J. App. Phys.* 61 1628–1632 (4) 1987, no month available.

Lindsey, J.S. et al. Rothemund and Adler–Longo Reactions Revisited: Synthesis of Tetraphenylporphyrins under Equilibrium Conditions *J. Org. Chem.* 52 pp. 827–836 1987, no month available.

Derwent Publications Ltd., London, JA 0284478 (Sanyo Chem Ind Ltd.), Dec. 15, 1986 (Abstract) 1986.

Abstract of patent, JP 61251842 1986, no month available.

Database WPI, Derwent Publications Ltd., London, GB; SU, A, 1098210 (Kutulya L A) Jun. 23, 1986. 1986.

Abstract of patent, JP 61–97025 1986, no month available.
Abstract of patent, JP 61–87760 1986, no month available.

Derwent Publications Ltd., London, DL 0234731 (Karl Marx Univ. Leipzig), Apr. 9, 1986. (Abstract) 1986.

Derwent World Patents Index, SU 1219612 (AS USSR Non–AQ Soln) Mar. 23, 1986. 1986.

Derwent Publications, Ltd., London, J6 1041381 (Osaka Prefecture), Feb. 27, 1986 (Abstract) 1986.

Dialog, JAPIO, JP 61–034057 (Ciba Geigy AG) Feb. 18, 1986. 1986.

Derwent World Patents Index, JP 61027288 (sumitomo Chem Ind KK) Feb. 6, 1986. 1986.

Sakai et al. "A Novel and Practical Synthetic Method of 3(3H)–Furanone Derivatives," *J. Heterocyclie Chem.* 23 pp. 1199–1201 1986, no month available.

Jellinek, H.H.G. et al. "Evolution of H20 and CO2 During the Copper–Catalyzed Oxidation of Isotactic Polypropylene," *J. Polymer Sci.* 24 389–403 1986, no month abailable.

Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986, no month available.

John J. Eisch and Ramiro Sanchez "Selective, Oxophilic Imination of Ketones with Bis (dichloroaluminum) Phenylimide" *J. Org. Chem.* 51 (10) 1848–1852 1986, no month available.

Derwent Publications Ltd., London, J6 0226575 (Sumitomo Chem Ind Ltd.), Oct. 11, 1985 (Abstract) 1985.

Abstract of patent, JP 60–156761 1985, no month available.

Derwent World Patents Index DE 344365 (Mitsubishi Yuka Fine Che. et al.) Jul. 11, 1985. abstract 1985.

Derwent Publications Ltd., London, J,A 0011451 (Fugi Photo Film KK), Jan. 21, 1985. (Abstract) 1985.

Derwent Publications, Ltd., London J6 0011449—A (Taoka Chemical KK) Jan. 21, 1985 (abstract) 1985.

Derwent World Patents Index JP 60–008088 (Mitsubishi Paper Mills Ltd.) Jan. 16, 1985. abstract 1985.

Roos, G. et al. "Textile applications of photocrosslinkable polymers" *Chemical Abstracts* 103 57 [no. 103:23690j] 1985, no month available.

Beck, M.T., et al. Mechanism of the autophotosensitized formulation of porphyrins in the reaction of pyrrole and m–disulfonated *Chemical Abstracts* 109 5:45 362 1985, no month available.

Derwent World Patents Index, EP 127574 (Ciba Geigy AG), Dec. 5, 1984 1984.

Derwent Publications Ltd., London, JP 1098187 (Canon KK), Nov. 9, 1984. (Abstract) 1984.
Derwent Publications Ltd., London, J,A, 0169883 (Ricoh KK), Sep. 25, 1984. (Abstract) 1984.
Derwent Publications Ltd., London, JA 0169883 (Ricoh KK), Sep. 25, 1984 (Abstract) 1984.
Derwent Publications Ltd., London, JA 0198187 (Canon KK), Nov. 9, 1984 (Abstract) 1984.
Derwent Publications Ltd., London, J,A, 0053563 (Dainippon Toryo KK), Mar. 28, 1984. (Abstract) 1984.
Derwent Publications Ltd., London, J,A, 0053562 (Dainippon Toryo KK), Mar. 28, 1984. (Abstract) 1984.
Derwent Publications Ltd., London, J,A, 0053562 (Dainippon Toryo KK), Mar. 28, 1984. (Abstract) 1984.
Abstract of Patent, JA 0053563 (Dainippon Toryo KK), Mar. 28, 1984 (Abstract) 1984.
Abstract of Patent, JA 0053562 (Dainippon Toryo KK), Mar. 28, 1984 (Abstract) 1984.
Derwent Publications Ltd., London, J,A, 0051961 (Dainippon Toryo KK), Mar. 26, 1984). (Abstract) 1984.
Abstract of Patent, JA 0051961 (Dainippon Toryo KK), Mar. 26, 1984 (Abstract) 1984.
Saenger, W. "Structural Aspects of Cyclodextrins and Their Inclusion Complexes" *Inclusion Compounds—Structural Aspects of Inclusion Compounds formed by Organic Host* 2 231–259 1984, no month available.
Szejtli "Industrial Applications of Cyclodextrins" *Inclusion Compounds: Physical Prop. & Applns* 3 331–390 1984, no month available.
Kano et al. "Three–Component Complexes of Cyclodextrins. Exciplex Formation in Cyclodextrin Cavity," *J. Inclusion Phenomena* 2 pp. 737–746 1984, no month available.
Suzuki et al. "Spectroscopic Investigation of Cyclodextrin Monomers, Derivatives, Polymers and Azo Dyes," *J. Inclusion Phenomena* 2, pp. 715–724 1984, no month available.
Abstract of Patent, JA 0222164 (Ricoh KK), Dec. 23, 1983 (Abstract) 1983.
Abstract of patent, JP 58211426 (Seikisui Plastics KK), (Dec. 8, 1983) 1983.
Derwent Publications, Ltd., London, EP0072775 (Ciba Geigy AG), Feb. 23, 1983 (Abstract) 1983.
van Beek, H.C.A. "Light–Induced Colour Changes in Dyes and Materials" *Color Res. and Appl.* 8 176–181 1983, no month available.
Connors, K.A. "Application of a stiochiometric model of cyclodextrin complex formation" *Chemical Abstracts* 98 598 [No. 98:53067g] 1983, no month available.
Abstract of Patent, EP 0065617 (IBM Corp.), Dec. 1, 1982 (Abstract) 1982.
Derwent Publications Ltd., London, J,A, 0187289 (Honshu Paper Mfg KK), Nov. 17, 1982. (Abstract) 1982.
Abstract of Patent, JA 0187289 (Honsho Paper Mfg KK), Nov. 17, 1982 (Abstract) 1982.
Abstract of Patent, JA 0185364 (Ricoh KK), Nov. 15, 1982 (Abstract) 1982.
Derwent Publications, Ltd., London J5 7139146 (Showa Kako KK) Aug. 27, 1982 (abstract) 1982.
Abstract of Patent, JA 0090069 (Canon KK), Jun. 4, 1982 (Abstract) 1982.
Derwent Publications, Ltd., London, JA 0061785 (Nippon Senka KK), Apr. 14, 1982 (Abstract) 1982.
Fischer, "Submicroscopic contact imaging with visible light by energy transfer" *Appl. Phys. Letter* 40(3) 1982, no month available.
Abstract of Patent, JA 0010659 (Canon KK), Jan. 20, 1982 (Abstract) 1982.
Abstract of Patent, JA 0010661 (Canon KK), Jan. 20, 1982 (Abstract) 1982.
Christen "Carbonylverbindungen: Aldehyde und Ketone," *Grundlagen der Organischen Chemie* 255 1982, no month available.
Derwent Publications Ltd., London, J,A, 0155263 (Canon KK), Dec. 1, 1981. (Abstract) 1981.
Abstract of Patent, JA 0155263 (Canon KK), Dec. 1, 1981 (Asbtract) 1981.
Abstract of Patent, JA 0147861 (Canon KK), Nov. 17, 1981 (Abstract) 1981.
Derwent Publications Ltd., London, J,A, 0143273 (Canon KK), Nov. 7, 1981. (Abstract) 1981.
Abstract of Patent, JP 56143272 (Canon KK), Nov. 7, 1981 (Abstract) 1981.
Patent Abstracts of Japan, JP 56143274 (Canon Inc.) Nov. 7, 1981, abstract. 1981.
Patent Abstracts of Japan, JP 56143274 (Canon Inc.) Nov. 7, 1981, abstract. 1981.
Abstract of Patent, JA 0136861 (Canon KK), Oct. 26, 1981 (Abstract) 1981.
Abstract of Patent, JA 6133378 (Canon KK), Oct. 19, 1981 (Abstract) 1981.
Abstract of Patent, JA 6133377 (Canon KK), Oct. 19, 1981 (Abstract) 1981.
Abstract of Patent, JA 6093775 (Canon KK), Jul. 29, 1981 (Abstract) 1981.
Derwent Publications Ltd., London, J,A, 0008135 (Ricoh KK), Jan. 27, 1981. (Abstract) 1981.
Derwent Publications Ltd., London, J,A, 0004488 (Canon KK), Jan. 17, 1981. (Abstract) 1981.
Abstract of Patent, JA 0004488 (Canon KK), Jan. 17, 1981 (Abstract) 1981.
Kirk–Othmer "Metallic Coatings," *Encyclopedia of Chemical Technology* 15 241–274 1981, no month available.
Komiyama et al. "One–Pot Preparation of 4–Hydroxychalcone β–Cyclodextrin as Catalyst," *Makromol. Chem.* 2 733–734 1981, no month available.
Derwent Publications, Ltd., London CA 1086–719 (Sherwood Medical) Sep. 30, 1980 (abstract) 1980.
Derwent Publications Ltd., Database WPI, JP 55 113036 (Ricoh KK), Sep. 1, 1980 1980.
Rosanske et al. "Stoichiometric Model of Cyclodextrin Complex Formation" *Journal of Pharmaceutical Sciences* 69 564–567 (5) 1980, no month available.
Rosanske et al. "Stoichiometric Model of Cyclodextrin Complex Formation" *Journal of Pharmaceutical Sciences* 69 564–567 (5) 1980, no month available.
Semple et al. "Synthesis of Functionalized Tetrahydrofurans," *Tetrahedron Letters* 81 pp. 4561–4564 1980, no month available.
Kirk–Othmer "Film Deposition Techniques," *Encyclopedia of Chemical Technology* 10 247–283 1980, no month available.
Derwent World Patents Index, Derwent Info. Ltd., JP 54158941 (Toyo Pulp KK), Dec. 15, 1979. (Abstract) 1979.
Derwent World Patents Index, JP 5411536 (Kawashima F) Sep. 12, 1979. 1979.
Derwent Publications Ltd., London, J,A, 0005422 (Fuji Photo Film KK), Jan. 16, 1979. (Abstract) 1979.
Drexhage et al. "Photo–bleachable dyes and processes" *Research Disclosure* 85–87 1979, no month available.

"Color imaging devices and color filter arrays using photo–bleachable dyes" *Research Disclosure* 22–23 1979, no month available.
Wolff, N.E., et al. "Electrophotography" *Kirk–Othmer Encyclopedia of Chemical Technology* 8 794–826 1979, no month available.
Derwent Publications Ltd., London, J,A, 0012037 (Pentel KK), Jan. 29, 1977. (Abstract) 1977.
Abstract of Patent, JA 0012037 (Pentel KK), Jan. 29, 1977 (Abstract) 1977.
Jenkins, P.W. et al. "Photobleachable dye material" *Research Disclosure* 18 [No. 12932] 1975, no month available.
Lamberts, R.L. "Recording color grid patterns with lenticules" *Research Disclosure* 18–19 [No. 12923] 1975, no month available.
Karmanova, L.S. et al. "Light stabilizers of daytime fluorescent paints" *Chemical Abstracts* 82 147 [no 59971p] 1975, no month available.
Prokopovich, B. et al. "Selection of effective photoinducers for rapid hardening of polyester varnish PE–250" *Chemical Abstracts* 83 131 [no 81334a] 1975, no month available.
"Variable Contrast Printing System" *Research Disclosure* 19 [No. 12931] 1975, no month available.
Lakshman "Electronic Absorption Spectrum of Copper Formate Tetrahydrate" *Chemical Physics Letters* 31 331–334 (2) 1975, no month available.
Derwent Publications, Ltd., London J4 9131–226 (TNational Cash Register C) Dec. 16, 1974 (abstract) 1974.
Chang, I.F., et al. "Color Modulated Dye Ink Jet Printer" *IBM Technical Disclosure Bulletin* 17(5) 1520–1521 1974, no month available.
"Darocur 1173: Liquid Photoinitiator for Ultraviolet Curing of Coatings" 1974, no month available.
Hosokawa et al. "Ascofuranone, an antibiotic from Ascochyta," Japan Kokai 73 91,278 (Nov. 28, 1973) *MERCK Index* 80 p. 283; abstract 94259t 1974, no month available.
Abstract of patent, NL 7112489 (Dec. 27, 1971). 1971.
Gafney et al. "Photochemical Reactions of Copper (II)—1, 3–Diketonate Complexes" *Journal of the Americqal Chemical Society* 1971, no month available.
Derwent Publications, Ltd., London SU 292698–S Jan. 15, 1971 (abstract) 1971.
Derwent World Patents Index,CS 120380 (Kocourek, Jan) Oct. 15, 1966. 1966.
Tsuda, K., et al. Vinyl Polymerization. CXLVI. The influence of dibenzoyl disulfide derivatives on radical polymerizations *Chemical Abstract* 196 6:29 198 1966, no month available.
R.T. Morrison & R.N. Boyd *Organic Chemistry* pp. 174; 707–711 1959, no month available.
Rigdon, J.E. "In Search of Paper that Spies Can't Copy" *Wall Street Journal*, no date available.
Chatterjee, S. et al. "Photochemistry of Carbocyanine Alkyltriphenylborate Satls: Intra–Iron–Pair Electron Transfer and the Chemistry of Boranyl Radicals" *J. Am. Chem. Soc.* 112 6329–6338, no date available.
"Assay—Physical and Chemical Analysis of Complexes" *AMAIZO*, no date available.
"Cyclodextrin" *AMAIZO*, no date available.
"Beta Cyclodextrin Polymer (BCDP)" *AMAIZO*, no date available.
"Chemically Modified Cyclodextrins" *AMAIZO*, no date available.
"Cyclodextrin Complexation" *American Maize Products Co.*, no date available.
"Monomers" *Scientific Polymer Products Inc.*, no date available.
Suppan, Paul "Quenching of Excited States" *Chemistry and Light* 65–69, no date available.
Yamaguchi, H. et al. "Supersensitization. Aromatic ketones as supersensitizers" *Chemical Abstracts* 53 107 (d), no date available.
Stecher, H. "Ultraviolet–absorptive additives in adhesives, lacquers and plastics" *Chemical Abstracts* 53 14579 (c), no date available.
Maslennikov, A.S. "Coupling of diazonium salts with ketones" *Chemical Abstracts* 60 3128e, no date available.
Derwent Publications Ltd., London, 4 9128022 no date available.
Abstract of Patent, JP 405195450, no date available.
Rose, Philip I. "Gelatin," *Encyclopedia of Chemical Technology* 7 488–513, no date available.

* cited by examiner

COLORANTS, COLORANT STABILIZERS, INK COMPOSITIONS, AND IMPROVED METHODS OF MAKING THE SAME

CROSS-REFERENCE TO RELATED APPLICATIONS

This patent application claims the benefit of priority to U.S. provisional patent application No. 60/116,315, filed on Jan. 19, 1999, and U.S. provisional patent application No. 60/121,301, filed on Feb. 23, 1999.

TECHNICAL FIELD

The present invention relates to an improved method for making porphines, and in particular 5,10,15,20-tetraphenyl-21H,23H-porphine-o,o$^1$,o$^{11}$,o$^{111}$-tetrasulfonic acid, tetrasodium salt (designated o-TPPS4). The present invention is also directed to a method of making Cu-meso-tetra-(2-sulfanatophenyl)-porphine (designated o-CuTPPS4) from o-TPPS4. The improved process allows the production of o-CuTPPS4 at lower cost and higher yields compared to conventional methods of making o-CuTPPS4. The present invention further relates to the use of o-CuTPPS4 as a colorant stabilizer for a variety of colorants, especially magenta colorants. The o-CuTPPS4, according to the present invention, provides a more stable and more "blue" colorant stabilizer compared to known colorant stabilizers, such as Cu-meso-tetra-(p-phenylcarboxylic acid)-porphine. The new porphine compounds may be used alone as a magenta dye or may be used in combination with one or more colorants to provide light stability to colorants. The present invention further relates to inks containing the new porphine compounds.

BACKGROUND OF THE INVENTION

U.S. patent application Ser. No. 08/757,222 filed Nov. 27, 1996, now U.S. Pat. No. 5,782,963; U.S. patent application Ser. No. 08/788,863 filed Jan. 23, 1997, now U.S. Pat. No. 6,099,628; U.S. patent application Ser. No. 08/843,410 filed Apr. 15, 1997, now U.S. Pat. No. 5,855,655; U.S. patent application Ser. No. 08/903,911 filed Jul. 31, 1997, now U.S. Pat. No. 5,891,229; and U.S. Provisional patent applications Ser. Nos. 60/055,785 filed Aug. 15, 1997, and 60/062,643 filed Oct. 22, 1997; all of which are assigned to Kimberly Clark Worldwide, Inc., disclose the use of a variety of porphines as colorant stabilizers. Porphines disclosed in the above-referenced applications include, but are not limited to, porphines having the following general structure:

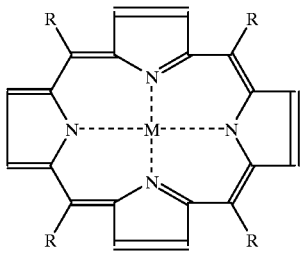

wherein R is any proton-donating moiety and M is iron, cobalt or copper. Desirably, R is SO$_3$H,

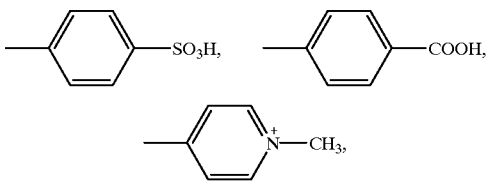

COOH, or R$_1$COOH wherein R$_1$ is an alkyl group of from 1 to 6 carbons. R may also be in its corresponding salt form, such as

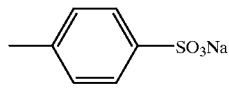

SO$_3$Na for SO$_3$H or

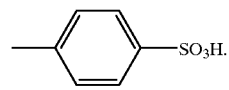

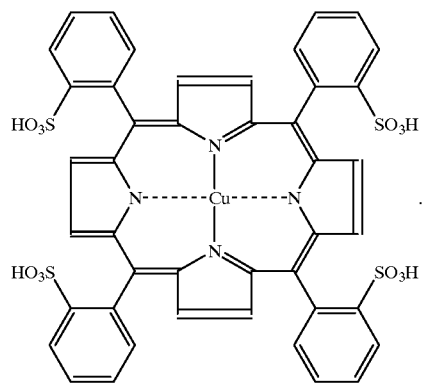

An attempt to make o-CuTPPS4 is disclosed in Treibs et al., *Leibigs Ann. Chem.*, 718, 183, 1998 (hereafter, "Treibs"). Treibs tried to prepare o-TPPS4 from 2-formylbenzenesulfonic acid, pyrrole, and propionoic acid. However, Treibs could not isolate the resulting product. Treibs reported a yield by GLC analysis of less than about 10%.

Although porphines provide excellent light stability to colorants, some porphines are relatively unstable and/or tend to "yellow" colorant compositions containing magenta dyes. A more desirable porphine molecule would be one that has less tendency to "yellow" a colorant composition, and moreover, to make the colorant composition more "blue."

Also, while the above-described porphines provide excellent colorant stability to one or more colorants associated with the porphines, they do not provide an orange/red color to a composition containing the porphines.

Accordingly, there exists a need in the art for a convenient, low cost, high yield method of making o-TPPS4, o-CuTPPS4, and compositions containing o-CuTPPS4. Further, there exists a need for improved porphines, which are capable of providing superior colorant stability while being more stable and without the tendency to "yellow" colorant compositions containing magenta dyes. Finally, there exists a need in the art for a new family of compounds that may be used alone as an orange/red colorant or may be used as a colorant stabilizer for one or more colorants associated with the new compounds.

SUMMARY OF THE INVENTION

The present invention addresses the needs described above by providing a new family of porphine compounds having the following general formula:

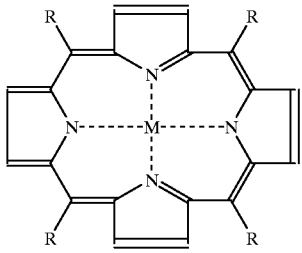

where M is iron, cobalt or copper; R represents

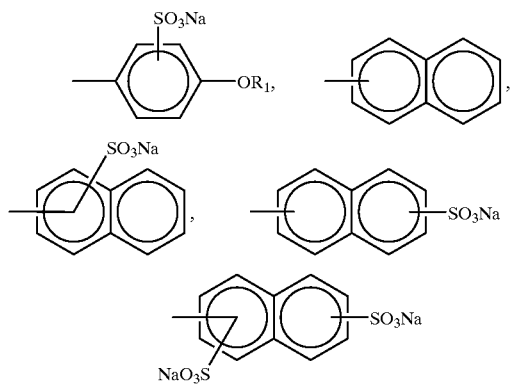

and $R_1$ represents an alkyl group having from 1 to 6 carbon atoms, an aryl group, or a substituted aryl group. The porphine compounds may be used as a magenta colorant and/or as a colorant stabilizer for other colorants. The new porphine compounds, when used as a colorant stabilizer, do not "yellow" magenta dyes. Consequently, unstable dyes, such as Acid Red 52, do not need to be used to make a magenta composition. The result is a more "blue" magenta color and a higher porphine to dye ratio, which creates superior light stability.

The present invention also addresses the needs described above by providing processes of making o-TPPS4 at a lower cost and higher yields. The present invention also relates to processes of making Cu-meso-tetra-(2-sulfanatophenyl)-porphine (designated o-CuTPPS4), and the use of o-CuTPPS4 as a colorant stabilizer for a variety of colorants, especially magenta colorants. o-CuTPPS4 has excellent stability and provides superior stability to a variety of colorants.

The present invention also relates to colorant compositions having improved stability, wherein the colorant is associated with one or more of the new porphine compounds. The present invention also relates to a process of making the new porphine compounds and the use of the porphine compounds in ink compositions.

These and other features and advantages of the present invention will become apparent after a review of the following detailed description of the disclosed embodiments and the appended claims.

DETAILED DESCRIPTION OF THE INVENTION

The present invention is directed to a new family of porphine compounds having the following general formula:

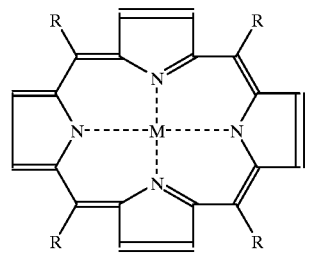

where M is iron, cobalt or copper; R represents

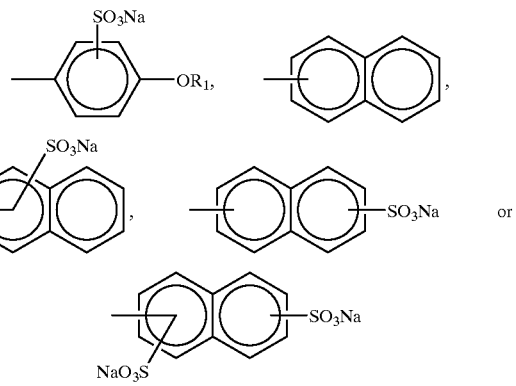

and where $R_1$ represents an alkyl group having from 1 to 6 carbon atoms, an aryl group, or a substituted aryl group. The new compounds may be used alone as a orange/red colorant or may be used as a colorant stabilizer.

In one embodiment of the present invention, the new porphine compound has one of the following structures:

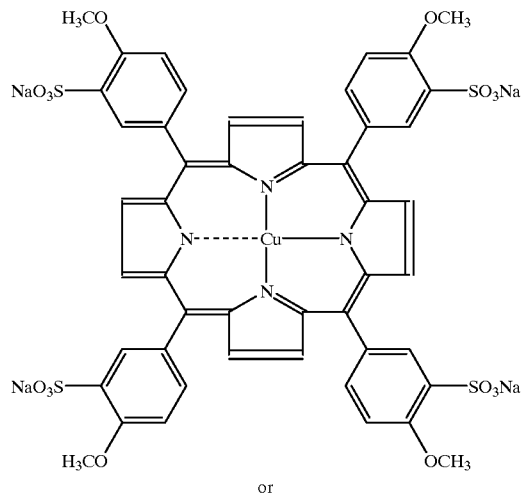

or

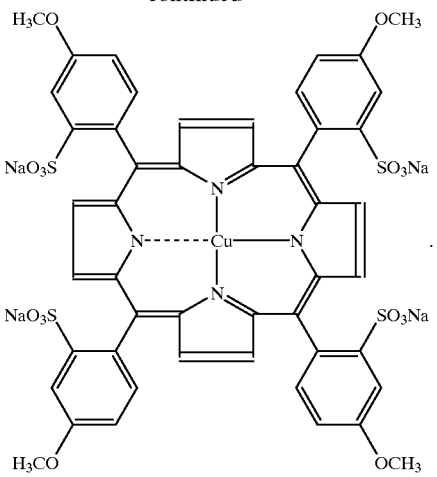

The present invention also relates to colorant compositions having improved stability, wherein the colorant is associated with one or more colorant stabilizers comprising the above-described porphine compounds. Desirably, one or more of the new porphine compounds are admixed with a colorant solution. The colorant stabilizer may be one or more of the new porphine compounds alone or in combination with at least one metal or metal salt. Suitable metals and metal salts are disclosed in U.S. Pat. No. 5,891,229, assigned to Kimberly Clark Worldwide, Inc., the entirety of which is incorporated herein by reference. Optionally, the new porphine compounds may be associated with a molecular includant, chelating agent, or other material to improve solubility and/or interaction of the porphine compound and the colorant. Suitable molecular includants, chelating agents, and other composition materials are also disclosed in U.S. Pat. No. 5,891,229, assigned to Kimberly Clark Worldwide, Inc., the entirety of which is incorporated herein by reference.

The new porphine compounds may be associated with a variety of dyes or colorants. A suitable dye or colorant, for example, may be an organic dye. Organic dye classes include, by way of illustration only, triarylmethyl dyes, such as Malachite Green Carbinol base {4-(dimethylamino)-_-[4-(dimethylamino)phenyl]-_-phenyl-benzene-methanol}, Malachite Green Carbinol hydrochloride {N-4-[[4-(dimethylamino)phenyl]phenyl-methylene]-2,5-cyclohexyldien-1-ylidene]-N-methyl-methanaminium chloride or bis[p-(dimethylamino)phenyl]phenylmethylium chloride}, and Malachite Green oxalate {N-4-[[4-(dimethylamino)-phenyl]-phenylmethylene]-2,5-cyclohexyldien-1-ylidene]-N-methyl-methanaminium chloride or bis[p-(dimethylamino)-phenyl]phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazino-carbonyl)amino]-2,3-dihydro-1,3-dioxo-1H-benz[de]iso-quinoline-5,8- disulfonic acid dilithium salt}; azine dyes, such as Janus Green B {3-(diethylamino)-7-[[4-(dimethyl-amino)phenyl]azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methyl-coumarin (4-methylumbelliferone); benzimidazole dyes, such as Hoechst 33258 [bisbenzimide or 2-(4-hydroxyphenyl)-5-(4-methyl-1-pipera-zinyl)-2,5-bi-1H-benzimidazole trihydro-chloride pentahydrate]; paraquinoidal dyes, such as Hematoxylin {Natural Black 1; 7,11b-dihydrobenz[b]-indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxy-benzene diazonium chloride, zinc chloride double salt); phenylenediamine dyes, such as Disperse Yellow 9 [N-(2,4-dinitrophenyl)-1,4-phenylenediarnine or Solvent Orange 53]; diazo dyes, such as Disperse Orange 13 [Solvent Orange 52; 1-phenylazo-4-(4-hydroxyphenylazo) naphthalene]; anthra-quinone dyes, such as Disperse Blue 3 [Celliton Fast Blue FFR; 1-methylamino-4-(2-hydroxyethylamino)-9, 1 0-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)-azo]-1-naphtha-lenyl)azo]-1,5-naphthalenedisulfonic acid tetrasodium salt}; xanthene dyes, such as 2,7-dichloro-fluorescein; proflavine dyes, such as 3,6-diamninoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29},N^{30},N^{31},N^{32}$]copper}; carotenoid dyes, such as trans-β-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracene-carbonylic acid); azure dyes, such as Azure A [3-amino-7-(dimethylamino) phenothiazin-5-ium chloride or 7-(dimethyl-amino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridine-diamine).

The present invention is further directed to a convenient, fast, low cost, environmental-friendly process of making new porphine compounds. One process of making new porphine compounds proceeds by the following reaction, wherein N,N-dimethylformamide (DMF) is used as the solvent:

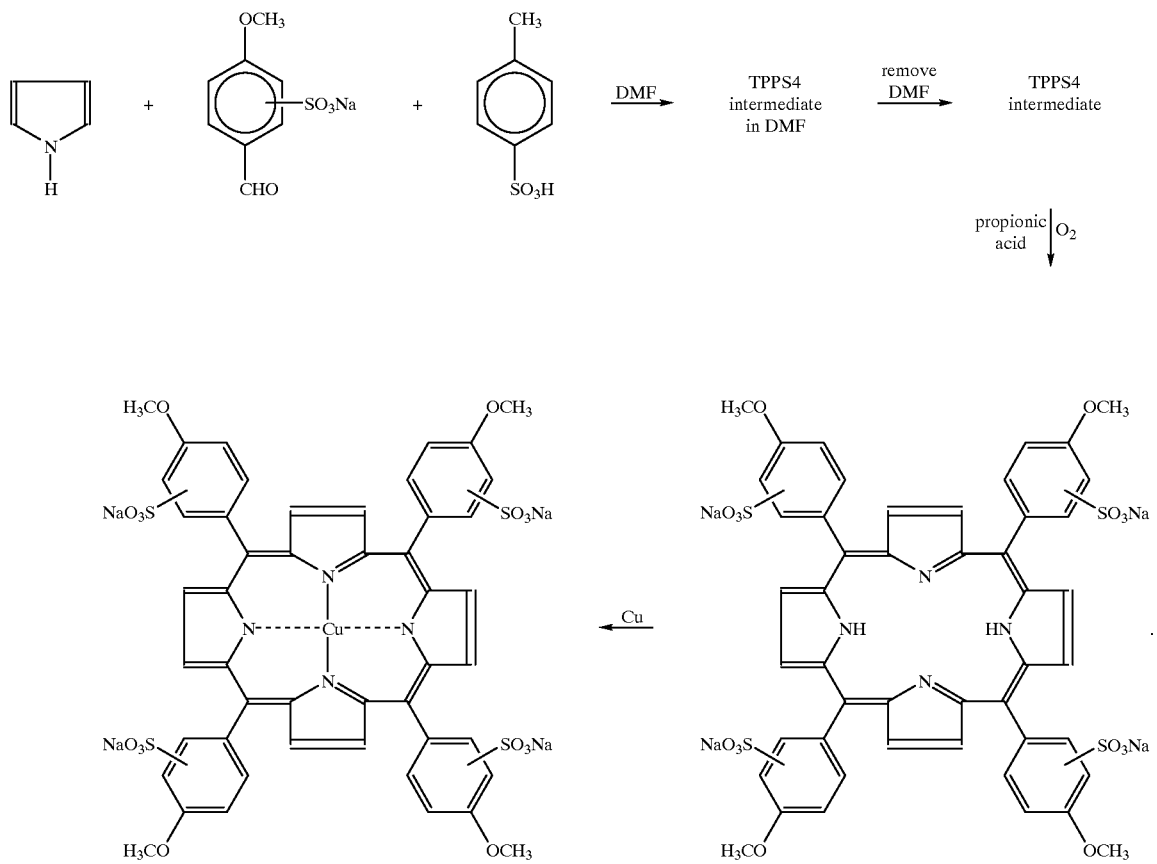

The above process produces TPPS4 at yields of greater than 80%, and as high as about 96 to 97%. The TPPS4 is further reacted with Cu to produce one of the porphine compounds of the present invention. The latter reaction proceeds at yields of greater than 90%, and as high as about 96 to 97%.

The reaction conditions for the above process may vary. Typically, the reaction may be carried out in a two-step process as follows. The reactants are purified by the following process or a similar purification process. The pyrrole is distilled under argon and a fraction is collected at 130° C. The substituted benzenesulfonic acid, sodium salt reactant is purified by a Dean and Stark method using benzene as the solvent. The solution is filtered at 60° C. and the solid pumped in a vacuum oven overnight at room-temperature. The p-toluene sulfonic acid may also be purified by a Dean and Stark method using benzene as the solvent. It should be noted that a variety of substituted benzenesulfonic acid, sodium salt reactants may be used in the above-described reaction. Suitable substituted benzenesulfonic acid, sodium salt reactants include, but are not limited to, 2-formylbenzenesulfonic acid, sodium salt; 3-formylbenzenesulfonic acid, sodium salt; 2-alkoxy-5-formylbenzenesulfonic acid, sodium salt; and 2-formyl-5-alkoxybenzenesulfonic acid, sodium salt; wherein the alkoxy group contains up to about six carbon atoms.

In the first step, the substituted benzenesulfonic acid, sodium salt, N,N-dimethylformamide (DMF) and pyrrole are placed in a reaction vessel and stirred at room-temperature. The mixture is flushed with argon for about five minutes while stirring prior to heating. The mixture is then heated to 100° C. for about ten to twelve minutes. The toluene sulfonic acid dissolved in 15 ml of DMF is injected into the reaction mixture. The reaction mixture is heated to 150° C. and held at this temperature for about 50 minutes to form a TPPS4 intermediate having an absorption peak at about 210 nm. DMF is removed from the reaction mixture to yield a precipitate.

In the second step, the TPPS4 intermediate is mixed with propionic acid. Air or oxygen is bubbled through the mixture at reflux for a period of time to yield a finished product having an absorption peak at about 412 nm. Conversion of the intermediate to the finished product may be monitored using an UV/VIS spectrometer. Reflux time may vary, but usually the reflux time is up to about 10 hours to convert the TPPS4 intermediate to TPPS4.

The choice of solvent in the first step of the above process may be any solvent, which enables the efficient production of TPPS4 and the new porphine compounds. Suitable solvents include, but are not limited to, DMF, dimethyl sulfoxide (DMSO), and dimethyl acetamide.

In a further embodiment of the present invention, porphine compounds, designated o-CuTPPS4, are produced by the following reaction, wherein DMF is used as the solvent:

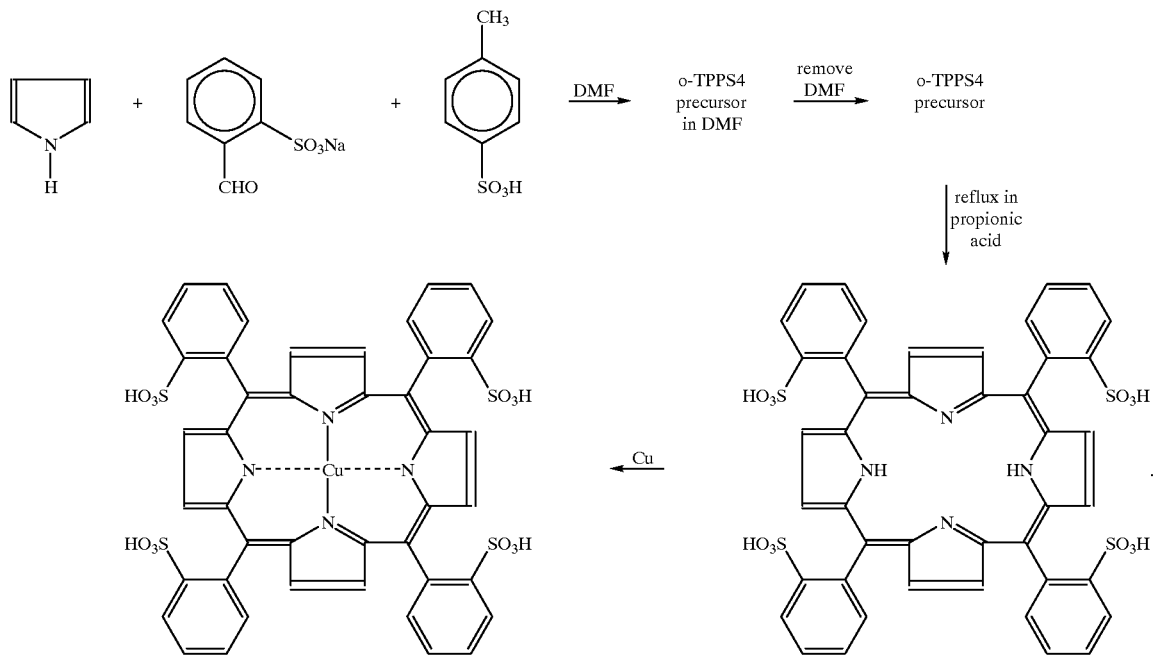

The above process produces o-TPPS4 at yields of greater than 90%, and as high as about 96 to 97%.

In this embodiment, the reactants are purified by the following process. The pyrrole is distilled under argon and a fraction is collected at 140° C. The 2-formylbenzenesulfonic acid, sodium salt and p-toluene sulfonic acid may each separately be purified by a Dean and Stark method using benzene as the solvent. The solution is filtered at 60° C. and the solid pumped in a vacuum oven overnight at room-temperature.

The reaction in this embodiment is also a two-step reaction. In the first step, the 2-formylbenzenesulfonic acid, sodium salt, N,N-dimethylformamide (DMF) and pyrrole are placed in a reaction vessel and stirred at room-temperature. The mixture is flushed with argon for about five minutes while stirring prior to heating. The mixture is then heated to 100° C. for about ten to twelve minutes. The toluene sulfonic acid dissolved in 15 ml of DMF is injected into the reaction mixture. The reaction mixture is heated to 150° C. and held at this temperature for about 50 minutes to form a o-TPPS4 precursor having an absorption peak at about 210 nm. DMF is removed from the reaction mixture to yield a precipitate.

In the second step, the o-TPPS4 precipitate is mixed with propionic acid. Air or oxygen is bubbled through the mixture at reflux for a period of time to yield a finished product having an absorption peak at about 412 nm. Conversion of the precursor to the finished product may be monitored using an UV/VIS spectrometer. Reflux time may vary, but usually the reflux time is up to about 10 hours to convert the o-TPPS4 precursor to o-TPPS4.

The present invention is further described by the examples which follow. Such examples, however, are not to be construed as limiting in any way either the spirit or scope of the present invention. In the examples, all parts are parts by weight unless stated otherwise.

EXAMPLE 1

Preparation of TPPS4 Intermediate

Tetra-(3-sulfanato-4-methoxyphenyl)-porphine (designated TPPS4) was prepared by mixing the following reactants in DMF solvent: pyrrole; 2-methoxy-5-formylbenzene sulfonic acid, sodium salt; and p-toluenesulfonic acid. Prior to mixing the reactants, pyrrole was distilled under an argon atmosphere with the fraction boiling at 130° C. collected. The 2-methoxy-5-formylbenzene sulfonic acid, sodium salt (Aldrich) was purified by a Dean and Stark method using benzene as the solvent. The solution was filtered at 60° C. and the resulting solid was pumped in a vacuum oven overnight at room-temperature. The DMF (99.9% anhydrous grade available from Aldrich) was used without further purification. The p-toluenesulfonic acid was purified by a Dean and Stark method using benzene as the solvent.

A mixture of 5.0 g of the pyrrole, 15.6 g of the 2-methoxy-5-formylbenzene sulfonic acid, sodium salt, and 200 ml of the DMF was placed into a 500 ml three-necked, round-bottom flask fitted with a magnetic stir bar, condenser, thermometer, and argon gas bubbler inlet. The reaction mixture was flushed with argon for five minutes with stirring prior to heating. The mixture was then heated to 100° C. for about 10–12 minutes at which time 0.76 g of p-toluenesulfonic acid was syringed into the reaction mixture. The p-toluenesulfonic acid was dissolved in 15 ml of DMF. The clear, colorless reaction mixture turned red to blood red to brown red to red black in one to two minutes. The reaction mixture was heated to 150° C. and held at this temperature for about 50 minutes.

After about 50 minutes at 150° C., the reaction was cooled in an ice bath for about 20 minutes. The DMF was removed to yield a precipitate. The wet solid was then placed in a vacuum oven overnight at ambient temperature to dry the solid.

EXAMPLE 2

Preparation of TPPS4 in an Argon Atmosphere

Ten grams of the dried powder of Example 1 was mixed with 200 ml of propionic acid in a 500 ml three-necked round-bottom flask. The mixture was heated at reflux in an argon atmosphere. The reaction mixture was monitored by a UV/VIS spectrometer to follow conversion of the TPPS4 intermediate to TPPS4.

The mixture was refluxed for about 67 hours to yield a small amount of TPPS4 having an absorption peak at 412 nm.

EXAMPLE 3

Preparation of TPPS4 in an Open Air Condenser

Ten grams of the dried powder of Example 1 was mixed with 200 ml of propionic acid in a 500 ml three-necked round-bottom flask. The mixture was heated at reflux with an open air condenser. The reaction mixture was monitored by a UV/VIS spectrometer to follow conversion of the TPPS4 intermediate to TPPS4.

The mixture was refluxed for about 67 hours. After 10 hours of reflux, conversion to TPPS4 was substantially completed. Full conversion to TPPS4 having an absorption peak at 412 nm was completed at 67 hours.

EXAMPLE 4

Preparation of TPPS4 with Air Bubbled Into the Reaction Mixture

Ten grams of the dried powder of Example 1 was mixed with 200 ml of propionic acid in a 500 ml three-necked round-bottom flask. The mixture was heated at reflux while air was bubbled into the reaction mixture. The reaction mixture was monitored by a UV/VIS spectrometer to follow conversion of the TPPS4 intermediate to TPPS4.

The mixture was refluxed for 10 hours. Full conversion to TPPS4 having an absorption peak at 412 nm was completed in 10 hours.

EXAMPLE 5

Preparation of CuTPPS4 Colorant Stabilizer

Cu-meso-tetra-(3-sulfanato-4-methoxyphenyl)-porphine (designated CuTPPS4) was prepared by the following reaction. A mixture of 0.31 g of copper, 5.0 g of TPPS4 from Example 4, and 50 ml of water were added to a 200 ml round-bottom flask fitted with a condenser and magnetic stirrer bar. The mixture was heated in reflux for three hours. The hot mixture was evaporated down to about 10 ml and chilled. Acetone was added to the mixture. The precipitate was filtered and washed with hexane and toluene. The precipitate was dried under vacuum to yield 3.9 g of a solid. The yield was about 72%.

TLC showed a clean product of CuTPPS4.

EXAMPLE 6

Preparation of a Magenta Composition Containing CuTPPS4 as the Colorant

A magenta ink was prepared having the following composition wherein the components are given in weight %:

|  | Red |
| --- | --- |
| DI Water | 82.69 |
| Borax | 1.90 |
| HCL(1N) | 1.57 |
| EDTA 2Na | 0.10 |
| CuTPPS4 (Example 5) | 0.50 |
| EG | 5.00 |
| Glycerine | 5.00 |
| GIV-GARD DXN ® | 0.20 |
| COBRATEC ® 99 | 0.10 |

The ink was prepared using the following components: deionized water; borax; hydrochloric acid as a buffer/pH adjuster; EDTA or sodium salts thereof as a chelating agent; ethylene glycol and glycerine as wetting agents; GIV-GARD DXN® as a biocide; COBRATEC® 99 as a corrosion inhibitor; and CuTPPS4 from Example 5 as the dye.

The magenta composition was printed onto a photoglossy medium to produce a light-stable magenta having color gamut with an enhanced blue component.

EXAMPLE 7

Preparation of a Magenta Composition Containing CuTPPS4 as a Colorant Stabilizer A magenta ink was prepared having the following composition wherein the components are given in weight %:

|  | Red |
| --- | --- |
| DI Water | 81.49 |
| Borax | 1.90 |
| HCL(1N) | 1.57 |
| EDTA 2Na | 0.10 |
| CuTPPS4 (Example 5) | 0.50 |
| EG | 5.00 |
| Glycerine | 5.00 |
| GIV-GARD DXN ® | 0.20 |
| COBRATEC ® 99 | 0.10 |
| Reactive Red 187 | 2.89 |
| Acid Red 52 | 1.20 |

The ink was prepared using the following components: deionized water; borax; hydrochloric acid as a buffer/pH adjuster; EDTA or sodium salts thereof as a chelating agent; ethylene glycol and glycerine as wetting agents; GIV-GARD DXN® as a biocide; COBRATEC® 99 as a corrosion inhibitor; Reactive Red 187 and Acid Red 52 as dyes; and CuTPPS4 from Example 5 as a colorant stabilizer.

The magenta composition was printed onto a photoglossy medium to produce a light-stable magenta having color gamut with an enhanced blue component.

EXAMPLE 8

Preparation of o-TPPS4 Precursor

Tetra-(2-sulfanatophenyl)-porphine (designated o-TPPS4) was prepared from the following reactants in a DMF solvent: pyrrole; 2-formylbenzene sulfonic acid, sodium salt; and p-toluenesulfonic acid. Prior to mixing the reactants, pyrrole was distilled under an argon atmosphere with the fraction boiling at 140° C. collected. The 2-formylbenzene sulfonic acid, sodium salt (Aldrich) was purified by a Dean and Stark method using benzene as the solvent. The solution was filtered at 60° C. and the resulting solid was pumped in a vacuum oven overnight at room-temperature. The DMF (99.9% anhydrous grade available from Aldrich) was used without further purification. The p-toluenesulfonic acid was purified by a Dean and Stark method using benzene as the solvent.

A mixture of 5.0 g of the pyrrole, 15.6 g of the 2-formylbenzenesulfonic acid, sodium salt, and 200 ml of the DMF was placed into a 500 ml three-necked, round-bottom flask fitted with a magnetic stir bar, condenser, thermometer, and argon gas bubbler inlet. The reaction mixture was flushed with argon for five minutes with stirring prior to heating. The mixture was then heated to 100° C. for about 10–12 minutes at which time 0.76 g of p-toluenesulfonic acid was syringed into the reaction mixture. The p-toluenesulfonic acid was dissolved in 15 ml of DMF. The clear, colorless reaction mixture turned red to blood red to brown red to red black in one to two minutes. The reaction mixture was heated to 150° C. and held at this temperature for about 50 minutes.

After about 50 minutes at 150° C., the reaction was cooled in an ice bath for about 20 minutes. The DMF was removed to yield a precipitate. The wet solid was then placed in a vacuum oven overnight at ambient temperature to dry the solid.

EXAMPLE 9

Preparation of o-TPPS4 in an Argon Atmosphere

Ten grams of the dried powder of Example 8 was mixed with 200 ml of propionic acid in a 500 ml three-necked round-bottom flask. The mixture was heated at reflux in an argon atmosphere. The reaction mixture was monitored by a UV/VIS spectrometer to follow conversion of the o-TPPS4 precursor to o-TPPS4.

The mixture was refluxed for about 67 hours to yield a small amount of o-TPPS4 having an absorption peak at 412 nm.

EXAMPLE 10

Preparation of o-TPPS4 in an Open Air Condenser

Ten grams of the dried powder of Example 8 was mixed with 200 ml of propionic acid in a 500 ml three-necked round-bottom flask. The mixture was heated at reflux with an open air condenser. The reaction mixture was monitored by a UV/VIS spectrometer to follow conversion of the o-TPPS4 precursor to o-TPPS4.

The mixture was refluxed for about 67 hours. After 10 hours of reflux, conversion to o-TPPS4 was substantially completed. Full conversion to o-TPPS4 having an absorption peak at 412 nm was completed at 67 hours.

EXAMPLE 11

Preparation of o-TPPS4 with Air Bubbled Into the Reaction Mixture

Ten grams of the dried powder of Example 8 was mixed with 200 ml of propionic acid in a 500 ml three-necked round-bottom flask. The mixture was heated at reflux while air was bubbled into the reaction mixture. The reaction mixture was monitored by a UV/VIS spectrometer to follow conversion of the o-TPPS4 precursor to o-TPPS4.

The mixture was refluxed for 10 hours. Full conversion to o-TPPS4 having an absorption peak at 412 nm was completed in 10 hours.

EXAMPLE 12

Preparation of o-CuTPPS4 Colorant Stabilizer

Cu-meso-tetra-(2-sulfanatophenyl)-porphine (designated o-CuTPPS4) was prepared by the following reaction. A mixture of 0.31 g of copper, 5.0 g of o-TPPS4 from Example 11, and 50 ml of water were added to a 200 ml round-bottom flask fitted with a condenser and magnetic stirrer bar. The mixture was heated in reflux for three hours. The hot mixture was evaporated down to about 10 ml and chilled. Acetone was added to the mixture. The precipitate was filtered and washed with hexane and toluene. The precipitate was dried under vacuum to yield 3.9 g of a solid. The yield was about 72%.

TLC showed a clean product of o-CuTPPS4.

EXAMPLE 13

Preparation of a Magenta Composition Containing o-CuTPPS4 Colorant Stabilizer

A magenta ink was prepared having the following composition wherein the components are given in weight %:

|  | Red |
| --- | --- |
| DI Water | 81.49 |
| Borax | 1.90 |
| HCL(1N) | 1.57 |
| EDTA 2Na | 0.10 |
| o-CuTPPS4 (Example 12) | 0.50 |
| EG | 5.00 |
| Glycerine | 5.00 |
| GIV-GARD DXN ® | 0.20 |
| COBRATEC ® 99 | 0.10 |
| Reactive Red 187 | 2.89 |
| Acid Red 52 | 1.20 |

The ink was prepared using the following components: deionized water; borax; hydrochloric acid as a buffer/pH adjuster; EDTA or sodium salts thereof as a chelating agent; ethylene glycol and glycerine as wetting agents; GIV-GARD DXN® as a biocide; COBRATEC® 99 as a corrosion inhibitor; Reactive Red 187 and Acid Red 52 as dyes; and o-CuTPPS4 from Example 12 as a colorant stabilizer.

The magenta composition was printed onto a photoglossy medium to produce a light-stable magenta having color gamut with an enhanced blue component.

Having thus described the invention, numerous changes and modifications thereof will be readily apparent to those having ordinary skill in the art, without departing from the spirit or scope of the invention.

What is claimed is:

1. An ink composition comprising a porphine having the following general formula:

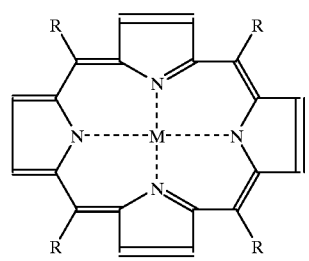

wherein M is iron, cobalt or copper; R represents

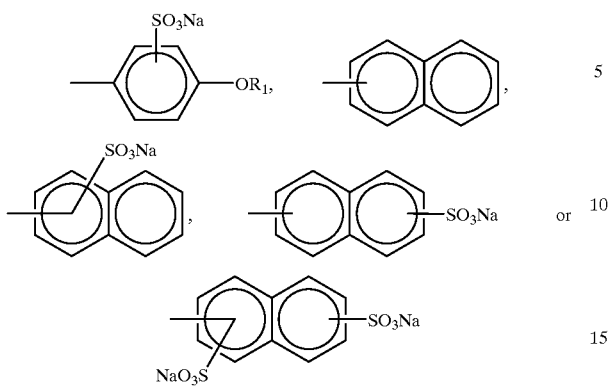

and $R_1$ represents an alkyl group having from 1 to 6 carbon atoms, an aryl group, or a substituted aryl group.

2. The ink composition of claim 1, wherein the composition further comprises one or more colorants.

3. The ink composition of claim 1, wherein the composition further comprises at least one metal or metal salt.

4. The ink composition of claim 3, wherein the metal or metal salt comprises a lanthanide or lanthanide salt.

5. The ink composition of claim 4, wherein the lanthanide or lanthanide salt comprises europium or europium salt.

6. The ink composition of claim 1, wherein the composition further comprises a colorant, a molecular includant, a chelating agent, or a combination thereof.

7. The ink composition of claim 6, further comprising a molecular includant.

8. The ink composition of claim 7, wherein the molecular includant is one or more cyclodextrins.

9. The ink composition of claim 8, wherein the one or more cyclodextrins comprise α-cyclodextrin, β-cyclodextrin, γ-cyclodextrin, δ-cyclodextrin, hydroxypropyl β-cyclodextrin, or hydroxyethyl β-cyclodextrin.

10. The ink composition of claim 1, wherein the porphine comprises

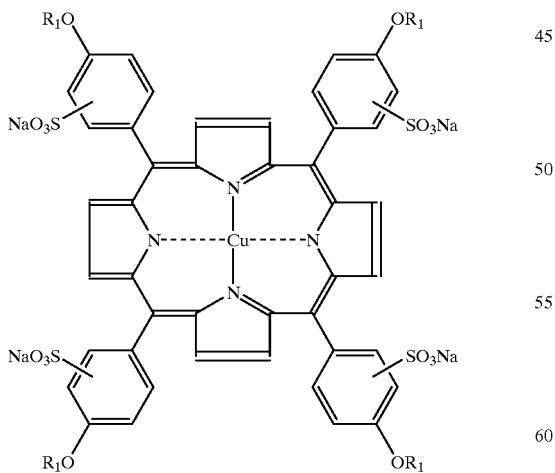

wherein $R_1$ represents an alkyl group having from 1 to 6 carbon atoms, an aryl group, or a substituted aryl group.

11. The ink composition of claim 1, wherein the porphine comprises

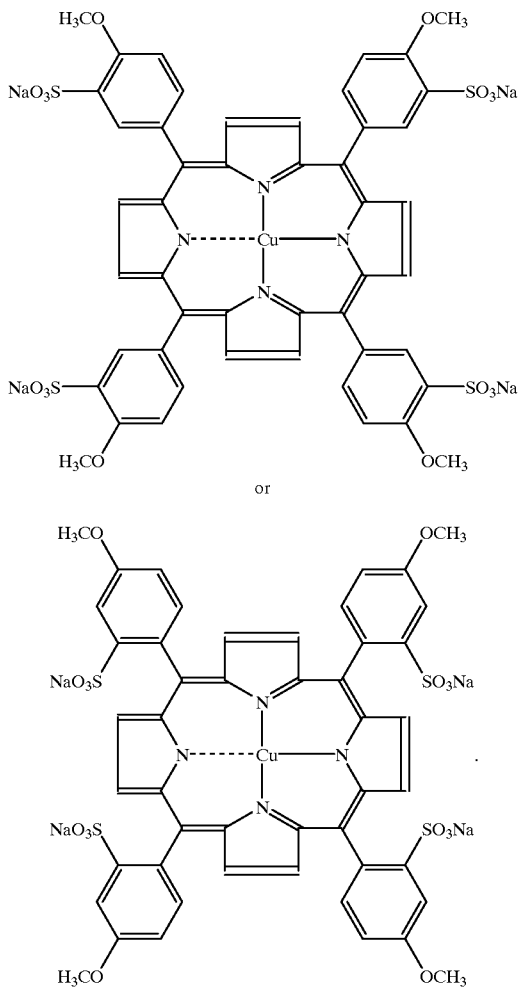

12. A porphine compound having the following structures:

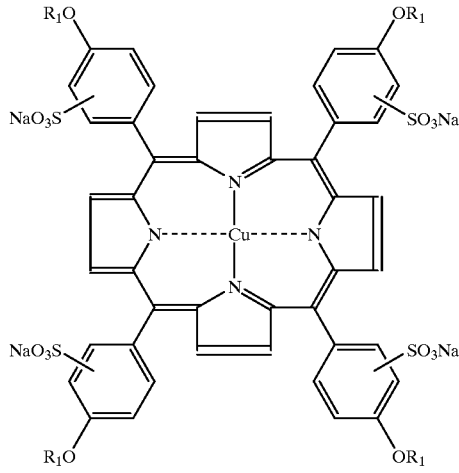

wherein $R_1$ represents an alkyl group having from 1 to 6 carbon atoms, an aryl group, or a substituted aryl group.

13. The compound of claim 12, wherein the compound has one of the following structures:

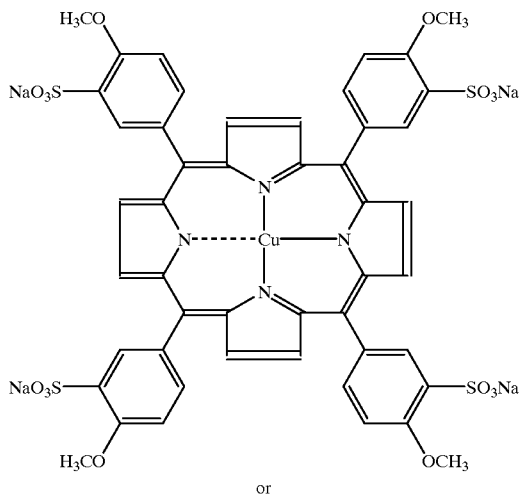

or

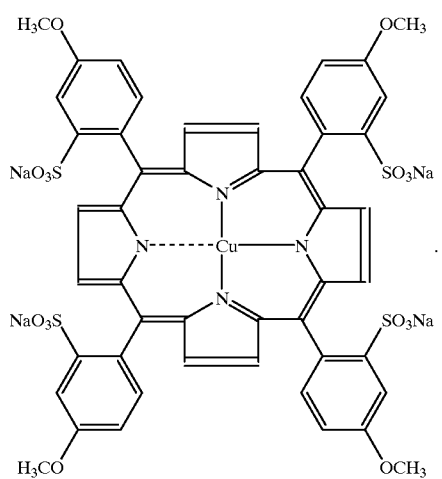

14. An ink composition comprising one of the porphine compounds of claim 13.

15. A method of making a porphine, said method comprising:
forming a first reaction mixture of a formyl-substituted benzenesulfonic acid or a sodium salt thereof, pyrrole, a substituted toluene compound, and a solvent;
heating the first reaction mixture to form a porphine precursor;
removing the solvent to yield a precursor precipitate;
mixing the precipitate with propionic acid to form a second reaction mixture;
heating the second reaction mixture at reflux to yield the porphine.

16. The method of claim 15, wherein the substituted benzenesulfonic acid comprises 2-formylbenzenesulfonic acid, 3-formylbenzenesulfonic acid, 4-formylbenzenesulfonic acid, 2-alkoxy-5-formylbenzenesulfonic acid, 2-formyl-5-alkoxybenzenesulfonic acid, or a salt thereof.

17. The method of claim 15, wherein the substituted toluene compound is p-toluenesulfonic acid or o-toluenesulfonic acid.

18. The method of claim 15, wherein the substituted benzenesulfonic acid comprises 2-formylbenzenesulfonic acid and the substituted toluene compound is p-toluenesulfonic acid.

19. The method of claim 15, wherein the solvent is dimethylformamide, dimethyl sulfoxide, or mixtures thereof.

20. The method of claim 19, wherein the solvent is dimethylformamide.

21. The method of claim 15, wherein the first reaction mixture is heated at about 150° C. for about one hour in an argon atmosphere.

22. The method of claim 15, wherein the porphine is further reacted with copper to produce Cu-meso-tetra-(4-sulfanatophenyl)-porphine or Cu-meso-tetra-(2-sulfanatophenyl)-porphine.

23. The method of claim 15, wherein the actual yield of the porphine is greater than about 90%.

24. The method of claim 23, wherein the actual yield of the porphine is about 96%.

25. The method of claim 15, wherein air is bubbled through the second reaction mixture during reflux.

26. The method of claim 15, wherein oxygen is bubbled through the second reaction mixture during reflux.

27. The method of claim 15, wherein the porphine comprises:

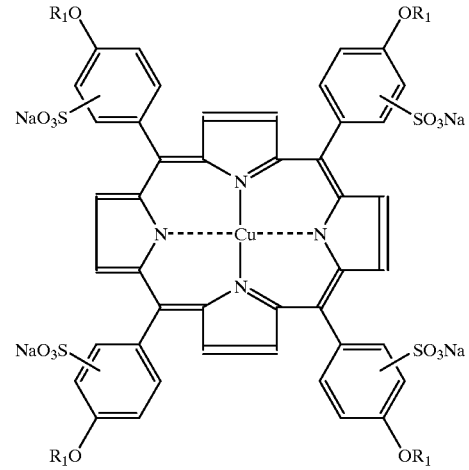

wherein $R_1$ represents an alkyl group having from 1 to 6 carbon atoms, an aryl group, or a substituted aryl group.

28. The method of claim 27, wherein the porphine comprises:

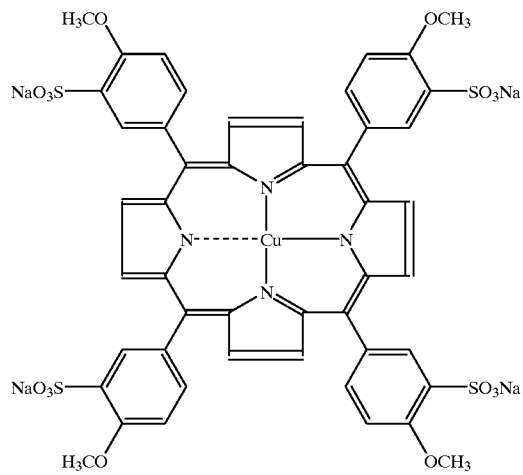

-continued
or
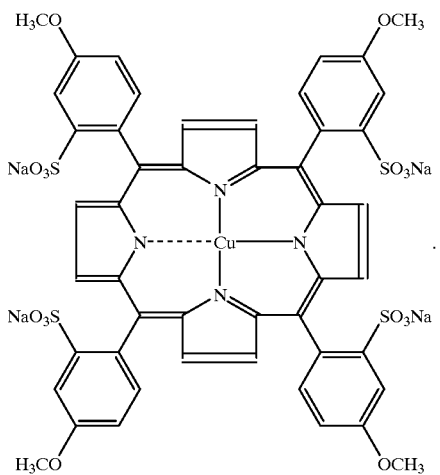
29. A method of light stabilizing a colorant, comprising associating the colorant with the porphine produced by the method of claim 15.
30. A method of making an ink comprising mixing a colorant with the porphine produced by the method of claim 15.
31. An ink composition comprising a colorant and the porphine produced by the method of claim 15.
* * * * *